(12) United States Patent
Yamamoto et al.

(10) Patent No.: US 8,394,111 B2
(45) Date of Patent: Mar. 12, 2013

(54) ENDOSCOPIC TREATMENT INSTRUMENT AND RETAINING DEVICE

(75) Inventors: Tetsuya Yamamoto, Hanno (JP);
Shotaro Takemoto, Tokyo (JP);
Tatsutoshi Hashimoto, Tokyo (JP);
Kiyotaka Matsuno, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1215 days.

(21) Appl. No.: 11/331,962

(22) Filed: Jan. 13, 2006

(65) Prior Publication Data
US 2007/0167978 A1    Jul. 19, 2007

(51) Int. Cl.
*A61B 17/04* (2006.01)
(52) U.S. Cl. .................. 606/144; 606/139
(58) Field of Classification Search ............. 606/144, 606/148, 139, 153, 205–209; 600/125, 127, 600/104–107, 129
See application file for complete search history.

(56) References Cited

U.S. PATENT DOCUMENTS

| | | | | |
|---|---|---|---|---|
| 3,090,386 | A * | 5/1963 | Babcock | 606/146 |
| 4,088,313 | A | 5/1978 | Pearson | |
| 4,935,027 | A * | 6/1990 | Yoon | 606/146 |
| 5,470,338 | A * | 11/1995 | Whitfield et al. | 606/144 |
| 5,575,800 | A | 11/1996 | Gordon | |
| 5,692,734 | A | 12/1997 | Aldredge, Sr. | |
| 5,735,849 | A | 4/1998 | Baden et al. | |
| 6,168,601 | B1 | 1/2001 | Martini | |
| 6,315,714 | B1 * | 11/2001 | Akiba | 600/114 |
| 6,338,475 | B1 | 1/2002 | Ping | |
| 6,988,987 | B2 * | 1/2006 | Ishikawa et al. | 600/114 |
| 7,338,502 | B2 * | 3/2008 | Rosenblatt | 606/139 |
| 2002/0116011 | A1 | 8/2002 | Chee Chung et al. | |
| 2003/0181924 | A1 | 9/2003 | Yamamoto et al. | |
| 2003/0216613 | A1 | 11/2003 | Suzuki et al. | |
| 2004/0147941 | A1 | 7/2004 | Takemoto et al. | |
| 2005/0234297 | A1 * | 10/2005 | Devierre et al. | 600/153 |
| 2006/0258905 | A1 * | 11/2006 | Kaji et al. | 600/106 |
| 2006/0282088 | A1 * | 12/2006 | Ryan | 606/144 |

FOREIGN PATENT DOCUMENTS

| | | |
|---|---|---|
| JP | 2002/159499 | 6/2002 |
| JP | 2003-225241 | 8/2003 |
| JP | 2005-161050 | 6/2005 |
| WO | WO 2005070282 | * 8/2005 |

OTHER PUBLICATIONS

United States Office Action dated Jun. 23, 2010.
U. S. Office Action dated Feb. 27, 2012 of related U.S. Appl. No. 11/652,824.

* cited by examiner

*Primary Examiner* — Julian Woo
*Assistant Examiner* — Christopher L Templeton
(74) *Attorney, Agent, or Firm* — Scully Scott Murphy & Presser, PC

(57) ABSTRACT

The endoscopic treatment instrument includes an insertion portion; a treatment portion; and a control portion. The treatment portion includes a pair of forceps members; a tip cover; a distal end holding portion that is fixed to a distal end of the insertion portion; a distal end locking member that restrains a relative movement by locking the tip cover onto the distal end holding portion; and a distal end release member that is provided on an operational member by which the pair of forceps members is opened and closed and that releases an engagement made by the distal end locking member between the tip cover and the distal end holding portion at least when the pair of forceps members is closed.

22 Claims, 26 Drawing Sheets

ENDOSCOPIC TREATMENT INSTRUMENT AND RETAINING DEVICE

BACKGROUND OF THE INVENTION

1. Field of the Invention

The present invention relates to a treatment instrument for an endoscope, and more particularly, to a retaining device placed and retained in the interior of a body and an applicator used to retain the retaining device therein.

2. Description of the Related Art

An abdominal operation in which a medical procedure is performed by largely incising the abdominal wall, a laparoscopic surgery in which a medical procedure is performed by approaching the abdominal cavities through an incision formed in the abdominal wall, or an endoscopic procedure in which a desired treatment is performed by inserting a flexible endoscope into the body through the mouth or the anus is conventionally known as a method for performing a medical procedure that deals with, for example, internal organs of the human body.

In the medical procedures using these methods, bodily tissues are sutured, tightly bound, or ligated. A retaining device that is placed and retained in a body is often used when such a treatment is performed. This type of retaining device is attached to an applicator, and is retained in a desired region of the body by operating the applicator from the interior of the body.

US Patent Application Publication No. 2003-0181924 A1 discloses an example of this type of retaining device and an applicator used to retain the retaining device (hereinafter, a "treatment instrument" is used as a general term for the retaining device and the applicator). The treatment instrument disclosed by this related art has the following structure. A detachable needle attached to a curved needle is inserted into bodily tissues, and then a hook sheath is moved toward the distal end of the instrument. Thereafter, the detachable needle is engaged by a casing engaged with the distal end. The hook sheath is then pulled toward the proximal end of the instrument, and the detachable needle is detached from the curved needle.

SUMMARY OF THE INVENTION

It is an object of the present invention to provide an improved endoscopic treatment instrument having higher operability.

The endoscopic treatment instrument according to a first aspect of the present invention includes an insertion portion having a distal end and a proximal end, the distal end being inserted into a body; a treatment portion provided at the distal end of the insertion portion; and a control portion provided at the proximal end of the insertion portion, and the treatment portion includes a pair of forceps members; a tip cover which supports a pivot shaft that pivots at least one of the pair of forceps members openably and closably with respect to the other forceps member; a distal end holding portion that is fixed to the distal end of the insertion portion and in which the tip cover is held relatively movably toward the distal end of the insertion portion and toward the proximal end of the insertion portion; a distal end locking member that restrains a relative movement by locking the tip cover onto the distal end holding portion when the pair of forceps members is opened to grasp a specified object; and a distal end release member that is provided on an operational member by which the pair of forceps members is opened and closed and that releases an engagement made by the distal end locking member between the tip cover and the distal end holding portion at least when the pair of forceps members is closed.

The endoscopic treatment instrument according to a second aspect of the present invention includes a casing holding portion that is provided at a distal end of an insertion portion to be inserted into a body and that holds a casing connected to a tip member by a thread, the casing containing the tip member detachably attached to one of a pair of forceps members after being passed through a tissue in response to a closing motion of the pair of forceps members at least one of which is pivoted openably and closably with respect to the other forceps member; a casing locking member which engages the casing holding portion and the casing together; and a guide member that is provided at the tip cover and that controls an engagement state made by the casing locking member between the casing holding portion and the casing.

The endoscopic treatment instrument according to a third aspect of the present invention includes a pair of forceps members; a tip cover which supports a pivot shaft that pivots at least one of the pair of forceps members openably and closably with respect to the other forceps member; a receiving portion that detachably holds a side of a distal end of an endoscope to be inserted into a body; and a regulating member that regulates a position of the distal end of the endoscope at a relative position with respect to the tip cover in order to restrict an amount of projection of the distal end of the endoscope with respect to the receiving portion.

The endoscopic treatment instrument according to a fourth aspect of the present invention includes a first sheath and a second sheath to a distal end of each of which a treatment portion used to perform treatment is connected and to a proximal end of each of which a control portion that operates the treatment portion is connected; a first holder which bundles the first sheath and the second sheath together; a second holder which bundles the first sheath and the second sheath together and that is provided nearer to the distal end than the first holder; a first adjusting member that provides sliding friction to the second sheath with respect to the first holder; and a second adjusting member that provides greater sliding friction than the first adjusting member to the first sheath with respect to the second holder.

The retaining device according to a fifth aspect of the present invention includes a string member that has an end and an opposite end; a tip member that is connected to the end of the string member; a thread locking member provided at the string member; a casing that has a space where the tip member and the thread locking member are contained and in which a tip-member locking member that is engaged with the tip member is provided; and a hole that is formed in the casing and into which a device that releases locking of the tip member by the tip-member locking member can be inserted.

DETAILED DESCRIPTION OF THE PREFERRED EMBODIMENTS

Embodiments of the present invention will be hereinafter described in detail with reference to the accompanying drawings.

Figure 1:
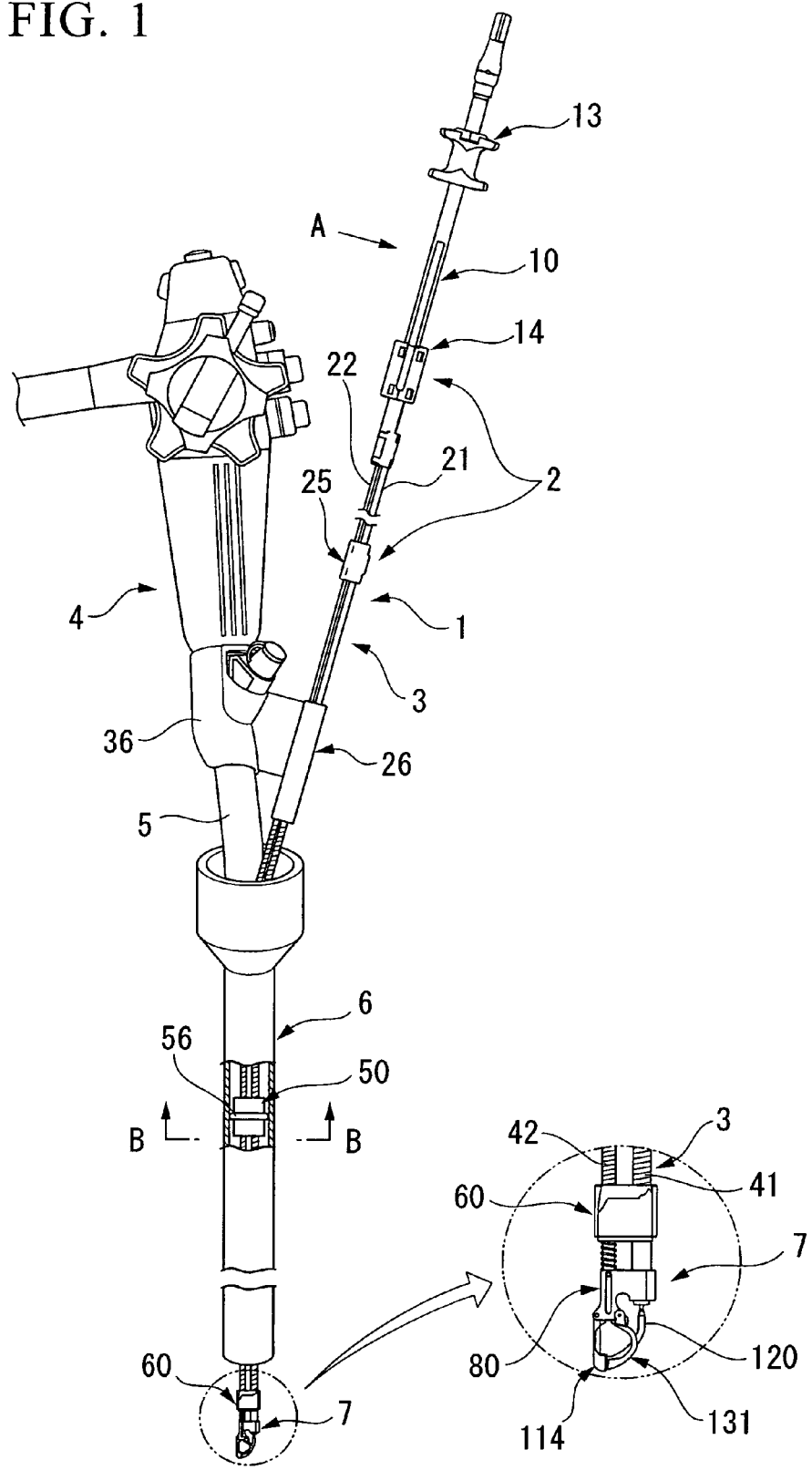
FIG. 1 is a view showing a schematic structure of a suture instrument which is an embodiment of an endoscope and an endoscopic treatment instrument.

FIG. 1 shows a suture instrument that is an example of an endoscopic treatment instrument. A suture instrument (applicator) 1 has a long insertion portion 3 extended from a control portion 2 that is operated by an operator. The insertion portion 3 is inserted in an overtube 6 together with an endoscope inserting part 5 of an endoscope 4. The tip of the insertion portion 3 projects from the distal end of the overtube 6. A treatment portion 7 is attached to the tip of the insertion portion 3.

Figure 2:
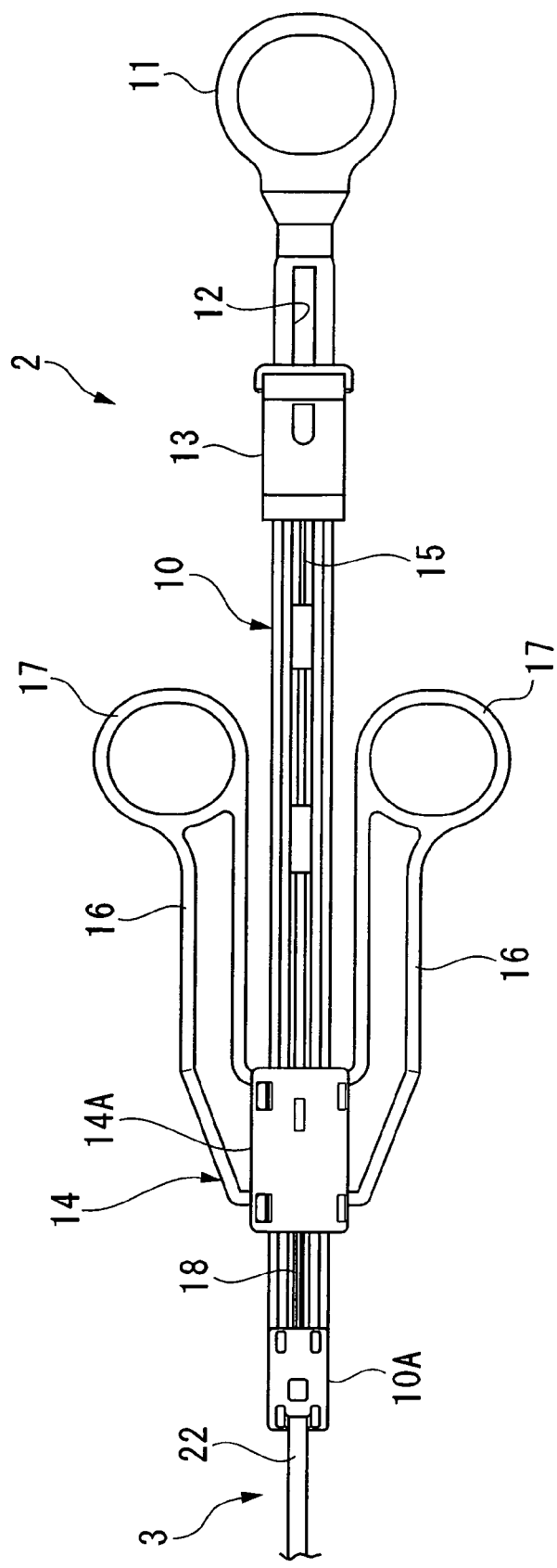
FIG. 2 is a view on arrow A in FIG. 1, showing a structure of a control portion.

As shown in FIG. 2, the control portion 2 has an elongated control body 10 that has a rigid shaft extending in an insertion direction. The insertion portion 3 extends from a distal end 10A of the control body 10. A finger-hook ring 11 is attached to the proximal end of the control body 10. A slit 12 is provided along a length direction of the control body 10 on the side nearer to the distal end than the ring 11. A forceps operating portion 13 and a hook operating portion 14, in order from the side of the ring 11, are attached to the slit 12 independently and slidably in the axial direction of the control body 10. ABS (acrylonitrile butadiene styrene) resin, polycarbonate, polyacetal, polyphenylsulfone, polyphthalamide, or polyether ether ketone can be mentioned as a material of the control portion 2. The instrument can be produced at low cost by making the control portion 2 of ABS resin, polycarbonate, or the like. Since slidability is increased by making the control portion 2 of polyacetal, a physical force required in operating the instrument can be reduced. Additionally, since excellent chemical resistance and excellent heat resistance can be obtained by making the control portion 2 of polyphenylsulfone, polyphthalamide, or polyether ether ketone, a change in quality caused by disinfection or sterilization becomes small.

A forceps operating wire (a forceps operating member, a first wire) 15 is fixed to the forceps operating portion 13. The forceps operating wire 15 is guided to the inside of the insertion portion 3 through the inside of the slit 12. In the hook operating portion 14, a pair of handles 16 extend from a side of a cylinder 14A toward the proximal end, and a finger-hook ring 17 is formed integrally with the base of the handle 16. The interval between the pair of handles 16 is large enough to allow the entry of the forceps operating portion 13. The hook operating portion 14 can have a long stroke by pulling the ring 17 of the handle 16 beyond the forceps operating portion 13. A hook operating wire (a hook operating member, a second wire) 18 is fixed to the hook operating portion 14. The hook operating wire 18 is guided to the inside of the insertion portion 3 through the inside of the slit 12. The number of the handles 16 may be one, or may be more than two.

Each of the control body 10, the forceps operating portion 13, and the hook operating portion 14 is made out of a resinous molded article, and are produced by fixing integrally-molded members in a snap-fit manner. In more detail, the control body 10 is produced by bending a developed member and then fixing this by a snap-fit connection. An independently molded ring 11 is fitted to the proximal end of the control body 10. Each of the forceps operating portion 13 and the hook operating portion 14 is produced by bending a developed member in such a way as to cover the control body 10 and then fixing this by a snap-fit connection.

Figure 3:
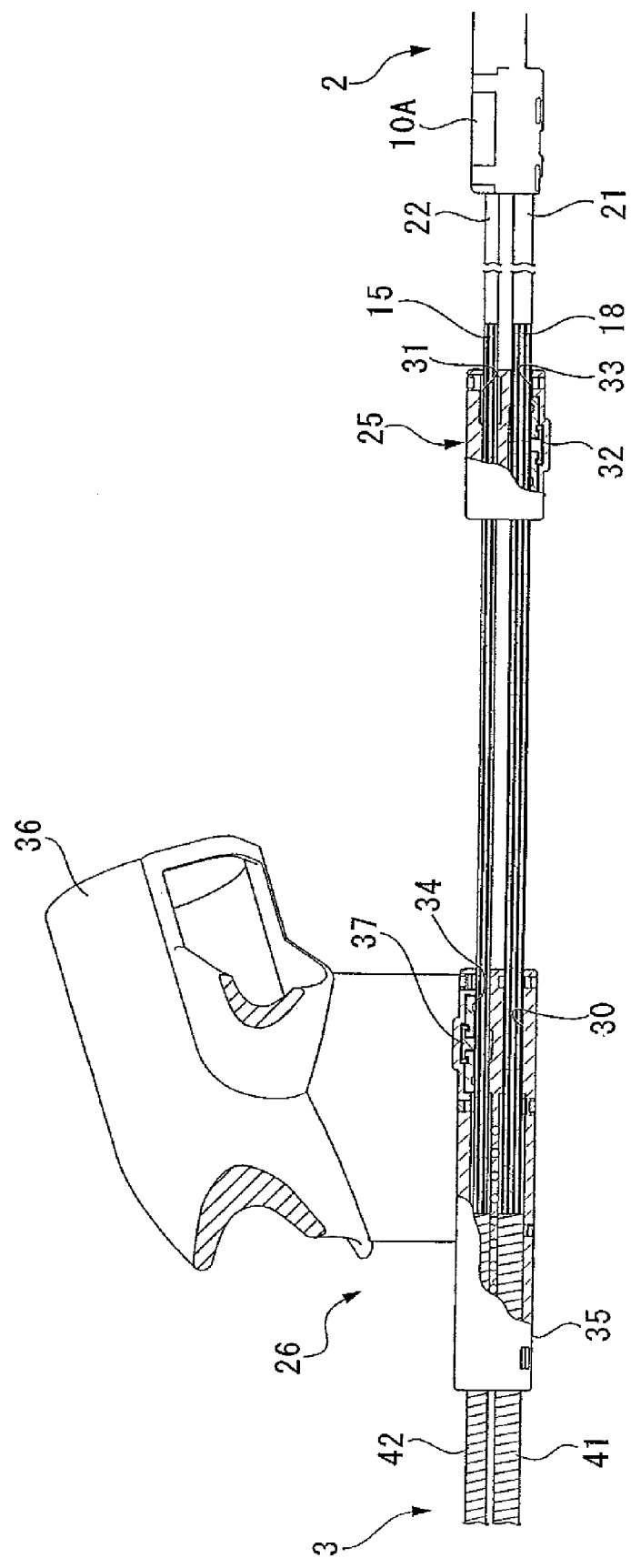
FIG. 3 is a partial sectional view showing a structure of an insertion portion.

As shown in FIG. 3, the insertion portion 3 has a hook sheath 21 extending from the distal end of the control portion 2 and a forceps sheath 22. The hook operating wire 18 is passed movably back and forth through the inside of the hook sheath 21. The forceps operating wire 15 is passed movably back and forth through the inside of the forceps sheath 22.

A movement control portion (a first holder) 25 that is a constituent of the control portion 2 and a scope holder (a second holder) 26 are disposed at the path of the insertion portion 3. The two sheaths 21 and 22 are bundled in parallel with each other by the movement control portion 25 and the scope holder 26. The movement control portion 25 has through-holes 30 and 31 that are formed in parallel with each other and through which the two sheaths 21 and 22 pass, respectively. A first adjusting member 32 is inserted in the through-hole 30 for the hook sheath 21 in such a way that its end projects therefrom. In this embodiment, a screw is used as the first adjusting member 32. The sliding friction of the hook sheath 21 is increased by tightening the first adjusting member 32 so as to come into contact with the hook sheath 21. On the other hand, the forceps sheath 22 is fixed to the movement control portion 25 in a state of being inserted in the through-hole 31.

The scope holder 26 has a holder body 35 having through-holes 33 and 34 that are formed in parallel with each other and through which the two sheaths 21 and 22 pass, respectively. A cylindrical receiving portion 36 through which the endoscope inserting part 5 of the endoscope 4 passes from the holder body 35 is formed integrally therewith. The through-hole 34 is formed in the scope holder 26. The forceps sheath 22 is inserted in the through-hole 34 movably back and forth. A second adjusting member 37 is disposed so as to come into contact with the forceps sheath 22. In this embodiment, a screw is used as the second adjusting member 37. The sliding friction of the forceps sheath 22 is increased by tightening the second adjusting member 37 so as to come into contact with the forceps sheath 22. On the other hand, no adjusting member is disposed at the through-hole 33 of the hook sheath 21 so as to be movable back and forth.

Both sheaths 21 and 22 proceed toward the scope holder 26 either by gripping the sheaths 21 and 22 exposed between the scope holder 26 and the movement control portion 25 or by advancing the movement control portion 25. Since the endoscope 4 held by the scope holder 26 does not move, the treatment portion 7 attached to the distal ends of both sheaths 21 and 22 can be advanced toward the endoscope 4.

On the other hand, when an operator intends to advance only the hook sheath 21, the hook sheath 21 is gripped to be advanced. At this time, the movement control portion 25 is not moved by the first adjusting member 32. The reason is that the sliding friction in the movement control portion 25 of the hook sheath 21 is small, and the sliding friction caused by the second adjusting member 37 in the scope holder 26 of the forceps sheath 22 is great, Therefore, the hook sheath 21 slides with respect to the movement control portion 25, and only the hook sheath 21 is advanced.

Thus, the movement control portion 25 and the scope holder 26 make it possible to properly use the sheaths 21 and 22 so as to advance both of the sheaths 21 and 22 or advance only the hook sheath 21. The sheaths 21 and 22 being operated can be more easily confirmed by making a difference in color between the hook sheath 21 and the forceps sheath 22, by making the surface of one of the sheaths 21 and 22 uneven, or by making a difference in outer diameter between the sheaths 21 and 22, in order to help the operator to operate the instrument.

The sliding friction caused by the first and second adjusting members 32 and 37 can be adjusted by an amount of tightening. According to another aspect, O rings may be used as the first and second adjusting members 32 and 37. If so, the sliding friction can be changed by the width of the O ring.

Each of the movement control portion 25 and the scope holder 26 is made out of a resinous molded article. The movement control portion 25 and the scope holder 26 are produced by fixing integrally-molded members with a snap-fit. In more detail, the movement control portion 25 and the scope holder 26 are produced according to the following way. The sheaths 21 and 22 are passed through grooves of developed members, which become the through-holes 30, 31, 33, and 34, and the first adjusting members 32 and 37 are inserted. Thereafter, the developed members are bent and fixed by a snap-fit connection.

The hook sheath 21 is inserted in a coil sheath 41. The forceps sheath 22 is inserted in a coil sheath 42. The two coil sheaths 41 and 42 extend forwardly from the scope holder 26. Each of the coil sheaths 41 and 42 is made out of a flat coil obtained by closely winding a flat metallic plate. From this structure, component cost can be reduced, and the number of assembling steps can be reduced, when compared to a conventional structure in which tubes are used. The outer surface of each of the hook sheath 21 and the forceps sheath 22 is covered with a heat-shrinkable tube made of low density polyethylene, high density polyethylene, or fluorine resin such as FEP or PFA, or the like. If the heat-shrinkable tube is made of low density polyethylene, the sliding friction with the coil sheaths 41 and 42 can be reduced, and, additionally, the heat-shrinkable tube can be produced at low cost. If the heat-shrinkable tube is made of high density polyethylene, the sliding friction can be reduced further. If the heat-shrinkable tube is made of fluorine resin such as FEP or PFA, a change in quality caused by disinfection or sterilization is slight, because the fluorine resin has small sliding friction and is superior in chemical resistance and heat resistance. The instrument can be operated with a small force by allowing each of the above examples to reduce sliding friction.

Figure 4:
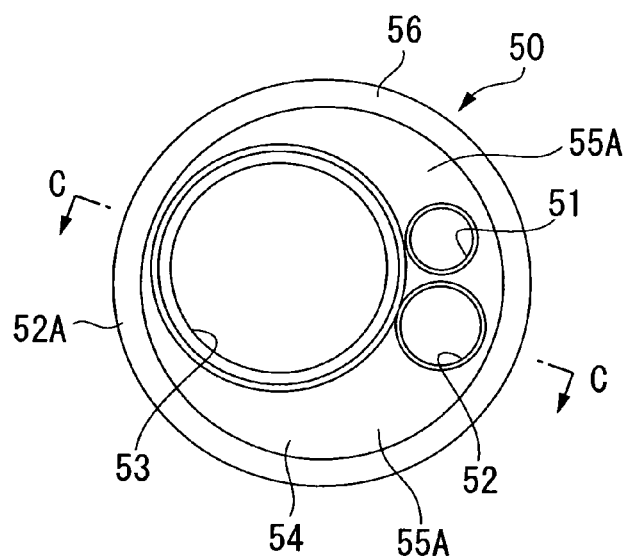
FIG. 4 is a view of a valving element along line B-B in FIG. 1.
Figure 5:
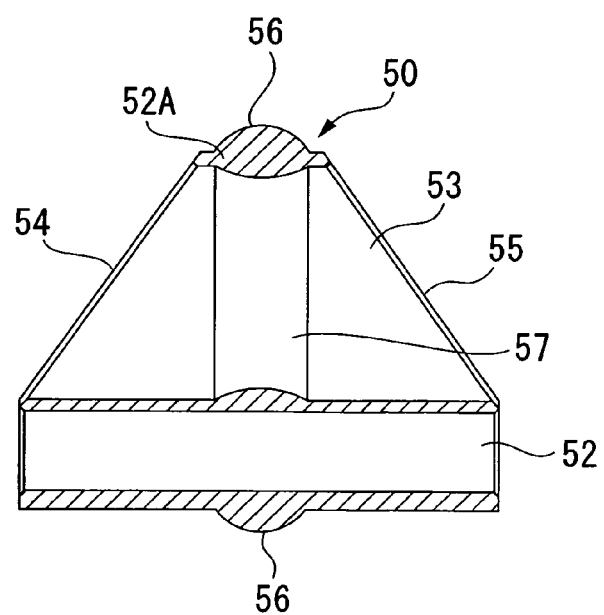
FIG. 5 is a sectional view along line C-C in FIG. 4.

As shown in FIG. 1, a valving element 50 which bundles the two coil sheaths 41 and 42 and the endoscope inserting part 5 of the endoscope 4 together and by which an airtight structure is formed between the valving element 50 and the overtube 6 is disposed midway on the insertion portion 3. Silicone rubber, natural rubber, or isopropylene rubber, or the like can be mentioned as a material of the valving element 50. The valving element 50 is fixed to the coil sheaths 41 and 42, for example, with an adhesive. As shown in FIG. 4 and FIG. 5, the valving element 50 has through-holes 51 and 52 for the sheaths 41 and 42 and a through-hole 53 for the endoscope 4 that are formed in parallel with each other. The valving element 50 has tapered surfaces 54 and 55 formed by slantingly cutting both end surfaces of a cylindrical member. The length in the insertion direction of a part 52A on the opposite side of the through-hole 52 is shortened by the tapered surfaces 54 and 55. A press-fit part 56, whose outer shape is a substantially circular arc when viewed cross-sectionally, is formed on the outer periphery of the valving element 50. A press-fit part 57 having the same shape as the press-fit part 56 is formed on the inner periphery of the through-hole 53 used for the endoscope 4. Since the tapered surfaces 54 and 55 are provided, the valving element 50 is not easily caught by the overtube 6. Since the press-fit part 56 is further provided, the valving element 50 comes into contact with the overtube 6 at only one place in the insertion direction. Therefore, from a decrease in contact area, the sliding friction is expected to be reduced, and it becomes easy to insert the endoscope inserting part 5. Likewise, since the press-fit part 57 makes a contact area with the endoscope inserting part 5 small, it becomes easy to insert the endoscope inserting part 5. Additionally, since the rigidity is improved by making a part 55A thick, the valving element 50 can be prevented from being deformed. Since the opening of each of the through-holes 51 to 53 is tapered to enlarge the outer diameter, the coil sheaths 41 and 42 and the endoscope inserting part 5 can be easily inserted.

Next, the treatment portion 7 will be described.

Figure 6:
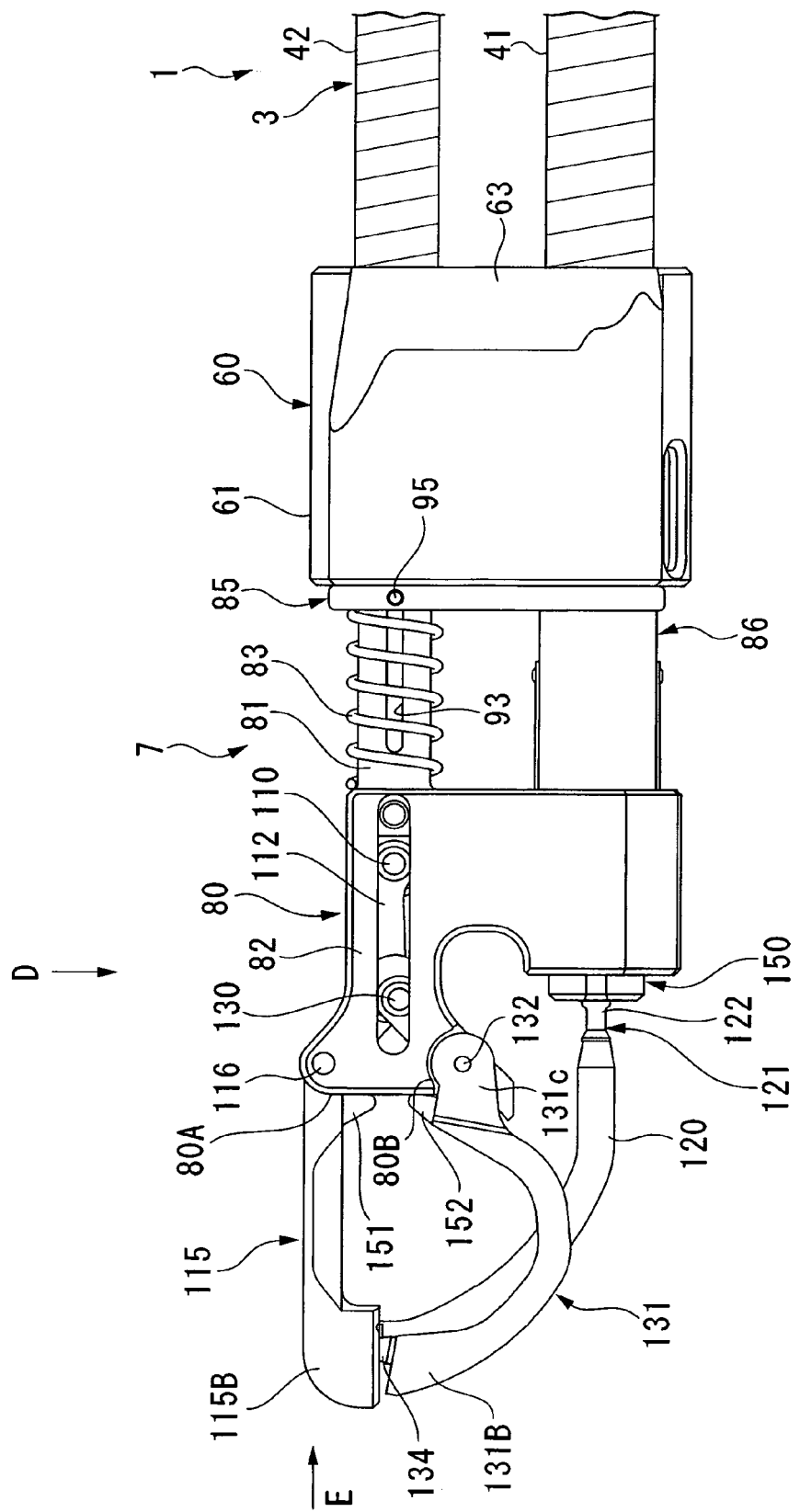
FIG. 6 is an enlarged view of a distal end of the suture instrument.
Figure 7:
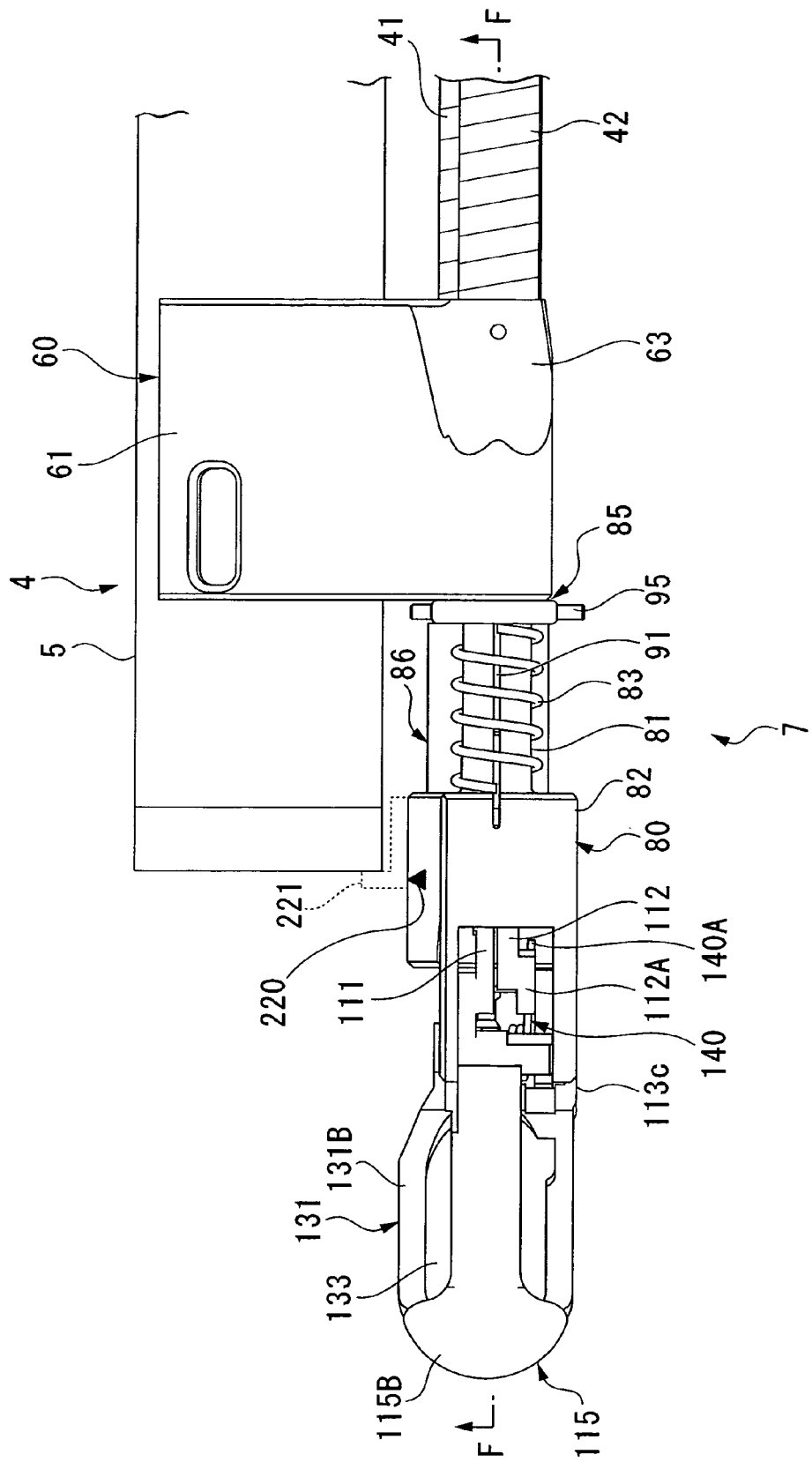
FIG. 7 is a view on arrow D in FIG. 6.
Figure 8:
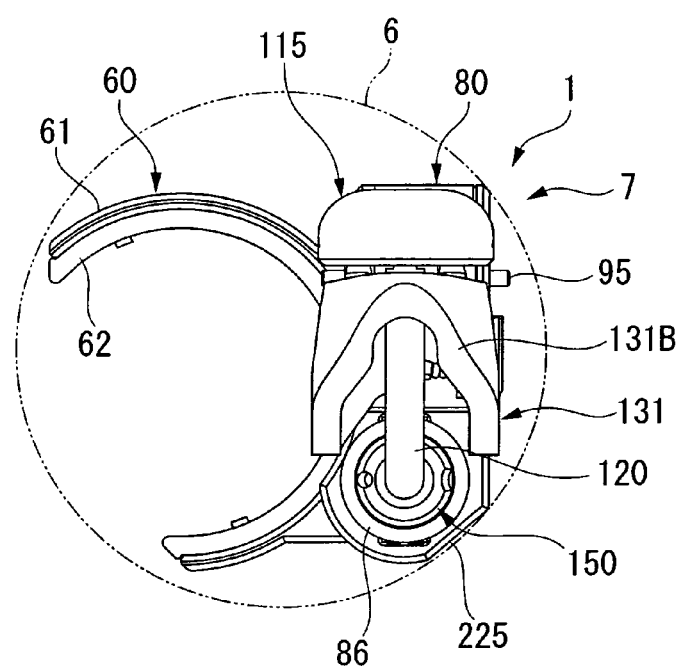
FIG. 8 is a view on arrow E in FIG. 6.

As shown in FIG. 6 to FIG. 8, a receiving portion 60 is fixed to the distal end of the insertion portion 3. As shown in FIG. 8, the receiving portion 60 has a C-shaped base 61 into which the endoscope inserting part 5 of the endoscope 4 can be inserted. Since a part of the base 61 is cut off, an outer shape obtained by combining the endoscope inserting part 5 and the suture instrument 1 together becomes small, and the diameter of the overtube 6 can be reduced. Additionally, a contact area between the receiving portion 60 and the overtube 6 can be reduced. From these, the insertion into the overtube 6 or into body cavities can be easily performed. To secure the connection strength between the base 61 and the endoscope 4, a flexible member 62 is affixed to the inner side of the base 61. The flexible member 62 additionally has a function to prevent the base 61 from damaging the endoscope 4.

As shown in FIG. 6 and FIG. 7, in the receiving portion 60, a taper portion 63 is formed at the proximal end toward which the coil sheaths 41 and 42 are pulled in. The taper portion 63 is formed to reduce the outer diameter of the receiving portion 60 toward the proximal end. As a result, the outer periphery of the base 61 is not caught by the taper portion 63 when the treatment portion 7 drawn out from the overtube 6 is again contained in the overtube 6 during manipulation.

Figure 9:
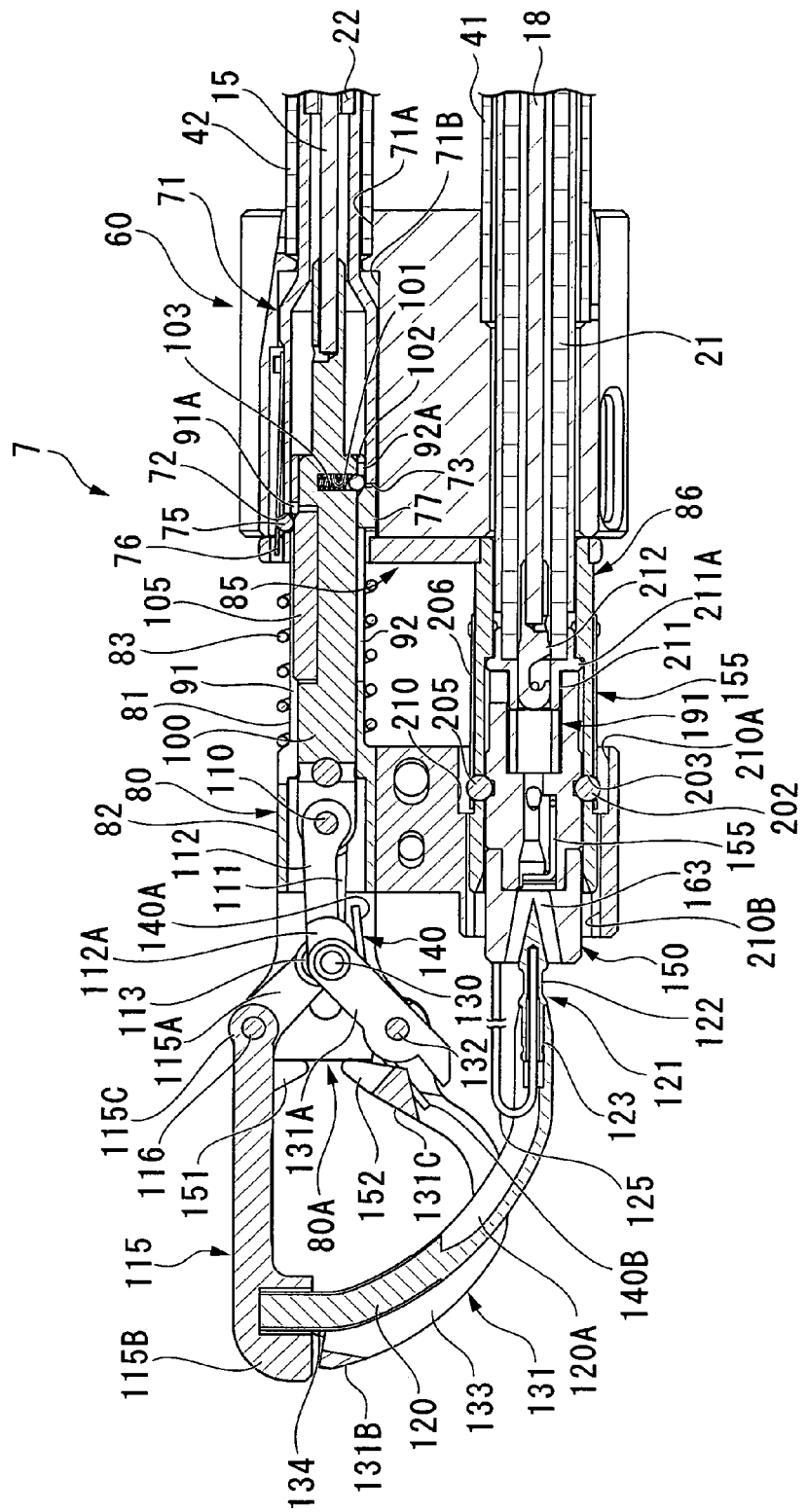
FIG. 9 is a sectional view along line F-F in FIG. 7.

As shown in FIG. 9, a cylindrical hole 71A to which the distal end of the coil sheath 42 is fixed on the outer periphery thereof is disposed in the receiving portion 60. A distal-end supporting member 71 is disposed movably back and forth in a hole 71B. The distal-end supporting member 71 extends along the axial line of the coil sheath 42. The forceps sheath 22 is fixed to the proximal end thereof, and the forceps operating wire 15 is passed through the inside thereof.

A hole 72 and a slit 73 are formed in the distal end of the distal-end supporting portion 71. The hole 72 and the slit 73 are formed on the straight line of the distal-end supporting portion 71, and an end of the slit 73 extends nearer to the proximal end than the hole 72. A pin 75 that is a first locking member (a distal-end locking member) is inserted in the hole 72. A part of the pin 75 projects into the distal-end supporting portion 71 in a state in which the pin 75 is inserted in the hole 72. The pin 75 is attached to the outer periphery of the distal-end supporting portion 71 by a leaf spring 76 serving as an urging member. The leaf spring 76 is urged in a direction in which the pin 75 is contained in the hole 72. On the other hand, an elongated release member 77 is inserted in the slit 73. The release member 77 is a second release member (a forceps release member) fixed to the distal-end supporting portion 71 by, for example, laser welding or by an adhesive. A proximal end of an elongated plate member and the distal-end supporting portion 71 in the direction of the center axis are slantingly cut.

A tube part 81 of a tip cover 80 is inserted in the distal-end supporting portion 71 from the side of the distal opening. The tip cover 80 has the tube part 81 that has the outer diameter substantially equal to the inner diameter of the distal-end supporting portion 71 and a cover body 82 formed integrally at the tip of the tube part 81. A coiled spring 83 is disposed outside the tube part 81. An urging force is applied so as to separate the cover body 82 from a bridge portion 85 fixed to the distal opening of the distal-end supporting portion 71. The bridge portion 85 extends in a direction perpendicular to the insertion direction. The tip of the distal-end supporting portion 71 is fixed to an end of the bridge portion 85, and the proximal end of a cartridge supporting member 86 described later is fixed to an opposite end of the bridge portion 85.

A plurality of slits 91, 92, and 93 are formed in the tube part 81 in the length direction. The slit 91 is formed according to the position at which the hole 72 of the distal-end supporting portion 71 is formed around the axial line of the tube part 81. The slit 91 has a width so as not to allow entry of the pin 75. However, only a base 91A of the slit 91 is increased in width, so that the tip of the pin 75 can enter the slit 91. The slit 92 is formed according to the position at which the slit 73 of the distal-end supporting portion 71 is formed around the axial line. The slit 92 has a width large enough to insert the release member 77. The base of the slit 92 extends nearer to the proximal end than the base 91A of the slit 91.

As shown in FIG. 6, the slit 93 is formed at a position where the other slits 91 and 92 are avoided. A pin 95 fixed to the bridge portion 85 is inserted in the slit 93 so as to be used as a slide guide of the tube part 81.

As shown in FIG. 9, a rod 100 that is a constituent of an opening and closing mechanism is inserted in the tube part 81 movably back and forth. The forceps operating wire 15 is fixed to the proximal end of the rod 100. A concave portion 101 extending in the radial direction is formed at a position near to the proximal end of the rod 100. A ball 102 serving as a second locking member (a forceps locking member) is inserted in the concave portion 101. The ball 102 is urged by a coiled spring 103 outwardly in the radial direction. The ball 102 can enter a large-diameter part 92A provided on the base of the slit 92 of the tube part 81, but cannot enter a more forward part than the large-diameter part 92A.

A release member 105 serving as a first release member (a distal-end release member) is provided at a position that is occupied more forwardly than the ball 102 and that is obtained by the rotation around the axial line by 180 degrees. The release member 105 projects at a position where the release member 105 coincides with the ball 102 around the rotational axis. The base of the release member 105 has a tapered surface by which the pin 75 can easily ride.

An end of each of two link members 111 and 112 is rotatably attached to the tip of the rod 100 via a pin 110. An opposite end of the link member 111 is rotatably attached to an end 115A of a forceps member 115 via a pin 113. The forceps member 115 has a bent part 115C between the end 115A of the forceps member 115 and an opposite end 115B thereof. The bent part 115C is rotatably pivoted on the tip cover 80 by means of a pin (pivot shaft) 116. A curved needle (attaching portion) 120 is fixed to the opposite end 115B of the forceps member 115. A detachable needle 121 is detachably attached to the tip of the curved needle 120. The detachable needle 121 has the pointed end part, a diameter-reduced contracted part 122 next to the pointed end part, and then a proximal end part 123. The proximal end part 123 is fitted to the curved needle 120. An end of a suture thread 125 is drawn in the proximal end part 123, and is fixed there. The contracted part 122 is formed when the suture thread 125 inserted therein is fixed while caulking concave parts formed on the detachable needle 121 from the four directions. According to this structure, the outer diameter of the detachable needle can be made smaller than a conventional detachable needle to which a suture thread is fixed by use of the knot of the suture thread. The suture thread 125 is drawn out through a slit 120A of the curved needle 120.

On the other hand, the opposite end of the other link member 112 is rotatably connected to the proximal end of an intermediate member 131A by means of a pin 130. The distal end of the intermediate member 131A is rotatably supported by the tip cover 80 via a pin 132. A forceps member 131 is rotatably pivoted on the tip cover 80 by means of the pin (pivot shaft) 132 on the side of the proximal end. A tip part 131B of the forceps member 131 is shaped like a ring having an opening 133, and is curved forwardly. A needle 134 that is inserted into tissues is fixed to the forefront of the forceps member 131.

Figure 10:
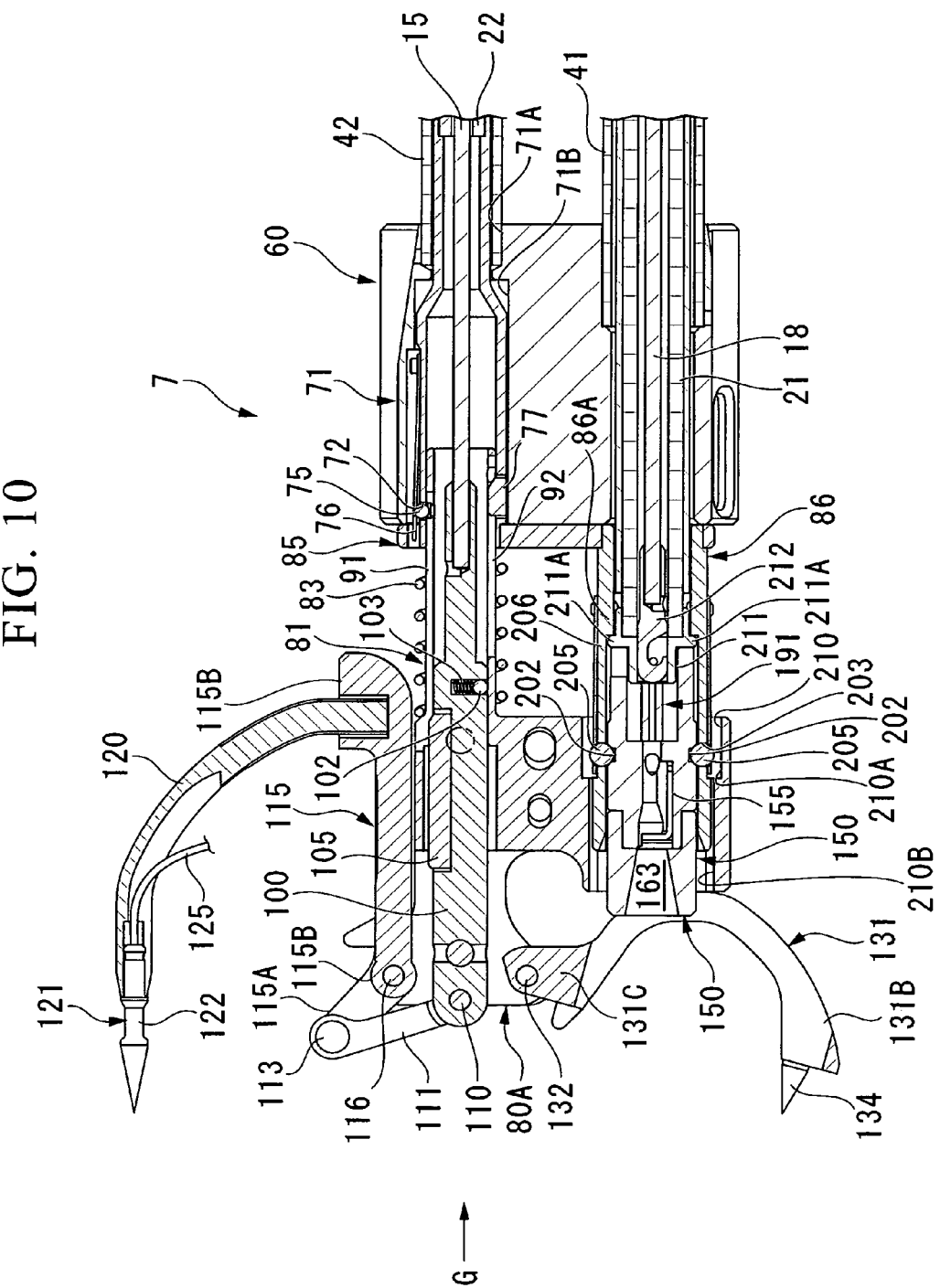
FIG. 10 is a sectional view obtained when a forceps member is opened.

As shown in FIG. 10, when the pair of forceps members 115 and 131 is opened, the tip of the detachable needle 121 attached to the curved needle 120 and the tip of the needle 134 of the forceps member 131 coincide with each other in the insertion direction. Since the needles 121 and 134 are inserted into tissues substantially simultaneously, the needles 121 and 134 do not easily come off from the tissues, and can be reliably inserted thereinto. Additionally, the needles 121 and 134 can be inserted deep thereinto.

As shown in FIG. 6, in the forceps member 131, a part 131C supported by the tip cover 80 via the pin 132 is disposed outside the tip cover 80. The tip cover 80 has a concave part 80B, and the part 131 C of the forceps member 131 is supported by the concave portion 80B via the pin 132. As shown in FIG. 7, a large difference in level does not exist at the boundary between the part 131 C of the forceps member 131 and the tip cover 80, and hence the endoscope can be easily inserted into the body cavities, and the operability is improved.

Additionally, since the forceps member 131 is supported outside the tip cover 80, a space used to dispose a charging spring that urges the forceps member 131 so as to be reliably closed is secured in the tip cover 80. As shown in FIG. 7 and FIG. 9, a charging spring 140 is wound like a coil with the pin 132 provided with a clearance. When the pair of forceps members 115 and 131 is closed, an end 140A of the charging spring 140 comes into contact with the proximal end of the intermediate member 131 A. An opposite end 140B of the charging spring 140 comes into contact with the part 131 C of the forceps member 131. When the pair of forceps members 115 and 131 is closed, the charging spring 140 applies an urging force so as to completely close the opposite end 131 B of the forceps member 131.

Figure 11:
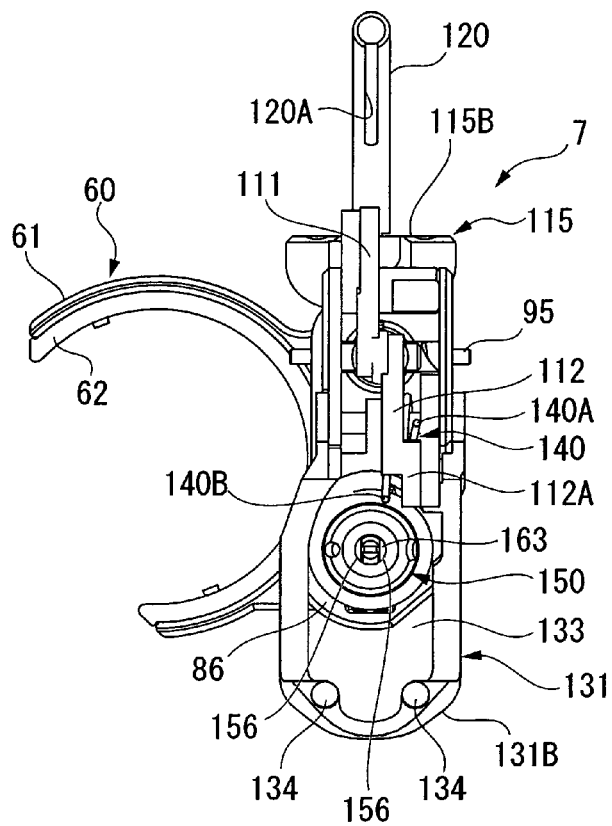
FIG. 11 is a view on arrow G in FIG. 10.

Since the charging spring 140 is wound like a coil, both of the ends 140A and 140B extend toward mutually different positions in the width direction. As shown in FIG. 11, the end 140A is disposed outside, whereas the opposite end 140B is disposed near the center. FIG. 11 shows a state in which the pair of forceps members 115 and 131 has been opened, and the charging spring 140 does not function. An opposite end 112A of the intermediate member 131A is expanded outwardly in the width direction so as to come into contact with the end 140A of the charging spring 140. On the other hand, the inside of the opposite end 112A of the intermediate member 131A is cut off, and the opposite end 112A thereof is deformed in the width direction. Since the opposite end 112A of the intermediate member 131A is structured in this way, interference between the intermediate member 131A and a casing 150 can be prevented when the casing 150 is moved back and forth. Additionally, in the structure to avoid the casing 150, adequate rigidity can be obtained by forming the deformed structure.

As shown in FIG. 6, the forceps members 115 and 131 are provided with projecting stoppers 151 and 152, respectively, that come into contact with a tip surface 80A of the tip cover 80 when the pair of forceps members 115 and 131 is completely closed. Since the stoppers 151 and 152 come into contact therewith, the forceps member 115 does not sag, and the axial line of the detachable needle 121 is not easily deviated when the pair of forceps members 115 and 131 is closed.

Next, a description will be given of the casing 150 into which the opposite end of the suture thread 125 is drawn as shown in FIG. 9 and the casing supporting portion 86 that supports the casing 150.

Figure 12:
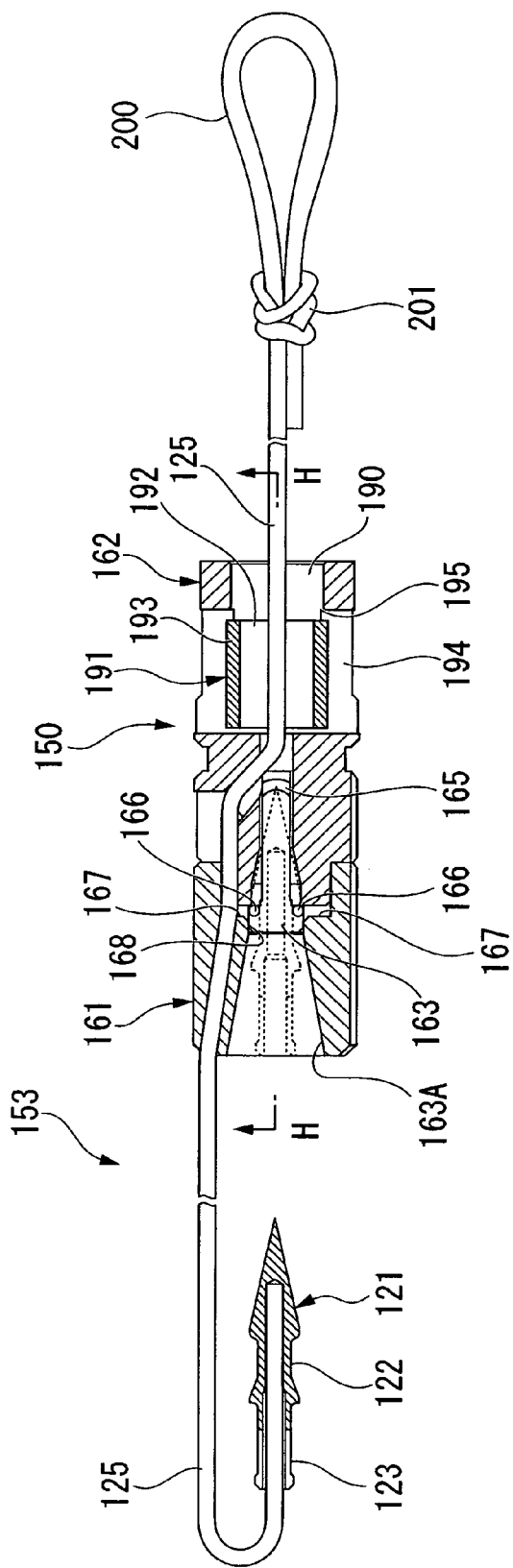
FIG. 12 is a sectional view showing a treatment instrument including a detachable needle, a casing, and a suture thread.
Figure 13:
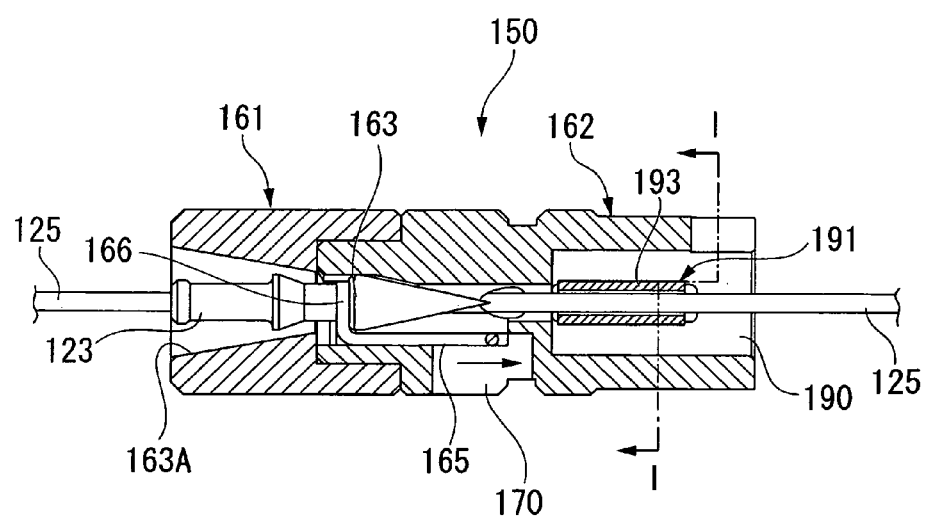
FIG. 13 is a sectional view along line H-H in FIG. 12, showing a state in which the detachable needle has been locked.

As shown in FIG. 12 and FIG. 13, the casing 150, the suture thread (string member) 125, and the detachable needle (tip member) 121 constitute a cartridge (also called a "retaining device") 153 that is retained in the body.

The casing 150 is formed by combining cylindrical members 161 and 162 together, and has a reception hole 163 into which the detachable needle 121 can be inserted. The distal end side of the reception hole 163 has a tapered surface 163A by which the axial line of the reception hole 163 and the axial line of the detachable needle 121 are allowed to easily coincide with each other. A wire spring 165, which is a needle locking member (tip-member locking member) used to prevent the detachable needle 121 from falling off, is inserted in the reception hole 163. The wire spring 165 is formed by bending a rod like the letter U and bending both ends 166 of the wire spring 165 by 90 degrees so as to become parallel in the same direction. The ends 166 of the wire spring 165 are disposed to reduce the width of the reception hole 163. In an initial state, the ends 166 of the wire spring 165 are contained in a groove 167 the width of which is greater than that of the reception hole 163. When the detachable needle 121 enters the reception hole 163, both ends 166 can be expanded. As shown in FIG. 13, when the detachable needle 121 is contained in the reception hole 163, the proximal end part 123 of the detachable needle 121 is completely contained in the casing 150. Therefore, tissues are never damaged by the proximal end part 123 of the detachable needle 121.

Polyphenylsulfone, polyphthalamide, polyether ether ketone, titanium alloy, or pure titanium can be mentioned as a material of the casing 150. If the casing 150 is made of polyphenylsulfone, polyphthalamide, or polyether ether ketone, the casing 150 does not easily undergo a change in quality in the living body, because they are superior in chemical resistance and acid resistance. Since these materials are also superior in welding, an assembling operation can be performed by use of ultrasonic wave welding or laser welding. Pure titanium or titanium alloy is superior in biocompatibility.

When the detachable needle 121 is contained in the casing 150, the wire spring 165 pinches the contracted part 122 of the detachable needle 121. If an operator intends to pull out the detachable needle 121 from the casing 150, the wire spring 165 is moved and slid together therewith, and the end 166 enters a narrow part 168 (see FIG. 12) on the distal-end side. Since the end 166 cannot be opened here, the wire spring 165 serves as a stopper, and prevents the detachable needle 121 from falling off. If the operator intends to pull out the detachable needle 121 from the casing 150, it is recommended to insert a release device into a release hole 170 formed in the side of the casing 150 and then return the wire spring 165 to the proximal end side as shown by the arrow in FIG. 13. As a result, the end 166 returns to the groove 167, whereby both ends 166 can be opened while being pushed. Therefore, the detachable needle 121 can be pulled out from the casing 150 by pulling the detachable needle 121 in a state of fixing the position of the wire spring 165.

Figure 14:
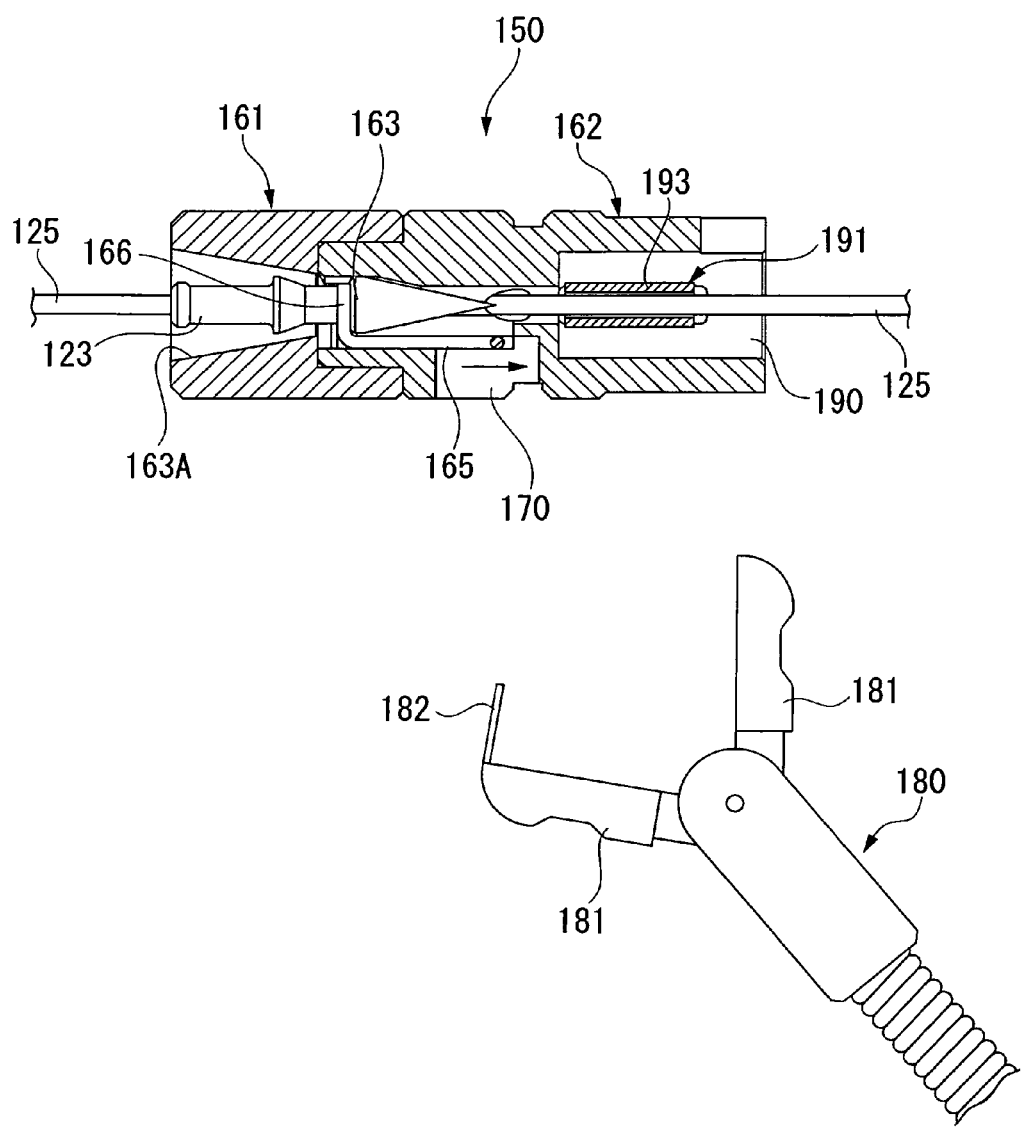
FIG. 14 is a view showing an example of a device for releasing the locking of the detachable needle.

For example, a device having a structure in which a holding member 181 of a forceps 180 is provided with a release pin 182 can be mentioned as the release device as shown in FIG. 14. If the operator inserts the release pin 182 through the release hole 170 by operating the instrument from the proximal end thereof, the detachable needle 121 can be pulled out from the casing 150 even during the manipulation. The form of the release device is not limited to that in FIG. 14. Any type of device can be employed as long as the device can be inserted through the release hole 170, and the wire spring 165 can be moved toward the proximal end side.

Figure 15:
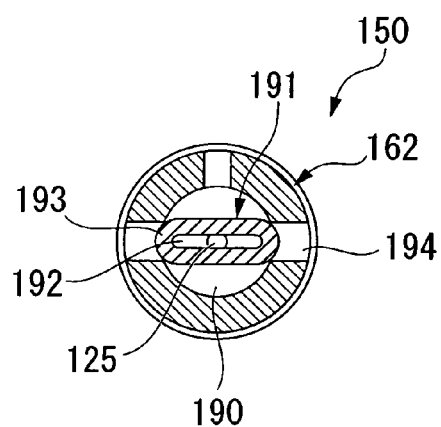
FIG. 15 is a sectional view along line I-I in FIG. 13.

As shown in FIG. 12 and FIG. 15, the suture thread 125 drawn into the casing 150 is pulled into the reception hole 163 from a position nearer to the proximal end than an area that the detachable needle 121 enters on the midway of the reception hole 163. The proximal end of the reception hole 163 leads to a large-diameter hole 190 formed in the surface of the proximal end of the casing 150. A brake portion (thread locking member) 191 is disposed inside the hole 190. The brake portion 191 has a flat shape obtained by winding a metallic plate 193 around an elastic member 192 through which the suture thread 125 is passed and then flattening the metallic plate 193. Predetermined sliding friction is generated between the suture thread 125 and the brake portion 191. The casing 150 has a slit 194 passing through the casing 150 in the radial direction. The brake portion 191 is loosely fitted to the slit 194. Since a step 195 formed between the hole 190 and the slit 194 functions as a stopper of the brake portion 191, the brake portion 191 never projects out of the casing 150 even when the brake portion 191 is pulled in the length direction of the suture thread 125. The brake portion 191 makes it possible to generate predetermined sliding friction when the casing 150 is moved between an end of the suture thread 125 and the opposite end thereof, and, as a result, the movement of the casing 150 is restrained.

Herein, the end of the suture thread 125 pulled out from the surface of the proximal end of the casing 150 forms a loop (hook catching portion) 200. A double, drawn-untied knot 201 is employed to form the loop 200. Since the double, drawn-untied knot 201 can make a knot of the loop 200 small, the loop 200 can be easily inserted into the hook sheath 21 even if the inner diameter of the hook sheath 21 is small.

As shown in FIG. 10, the casing 150 is contained in the casing supporting member 86. A ball (a third locking member, a casing locking member) 205 that is inserted through the hole 203 of the casing supporting member 86 is engaged with each annular concave portion 202 formed on the side of the casing 150. The ball 205 is urged to be fastened to the casing 150 by a leaf spring 206 serving as an urging member fixed to the casing supporting member 86. It is permissible to unite the ball 205 and the leaf spring 206 together by use of laser welding or an adhesive. The end of the casing supporting member 86 is inserted movably back and forth in a guide hole 210 used as a guide member of the tip cover 80. The guide hole 210 has its proximal end whose diameter has been increased. The ball 205 can be moved outwardly in the radial direction in a part 210A widened as shown in FIG. 9. A distal end part 210B is smaller in the diameter of the guide hole 210 than the diameter-increased part 210A, and hence the ball 205 cannot be moved outwardly in the radial direction.

In the casing supporting member 86, a distal claw portion 211 attached to the hook sheath 21 is fitted into the hole 190 of the casing 150. The distal claw portion 211 has a flange 211A that serves as a stopper by coming into contact, from the distal end side, with a step 86A formed on the inner periphery of the casing supporting member 86. A hook 212 is contained in the through-hole thereof. The hook 212 is fixed to the tip of the hook operating wire 18 passed movably back and forth through the hook sheath 21. The loop 200 (see FIG. 12) formed on the opposite end of the suture thread 125 is caught by the hook 212. Conventionally, an inner tube has been provided between the hook sheath 21 and the casing supporting portion 86. However, in this embodiment, the structure of the instrument is simplified by excluding the inner tube. As a result, component cost can be reduced, and the number of assembling steps can be reduced.

As shown in FIG. 7, a mark 220, which is used as a restriction part by which the endoscope 4 is positioned in the insertion direction, is provided on the side of the tip cover 80 of the treatment portion 7. A rigid part of the distal end of the endoscope 4 and a rigid part of the treatment portion 7 can be overlapped with each other in the insertion direction by putting the distal end of the endoscope 4 onto the mark 220. Conventionally, the distal end of the endoscope 4 has been positioned on the receiving portion 60, and hence the whole length of the rigid part is equal to the sum of the length of the treatment portion 7 and the length of the rigid part of the endoscope 4. Therefore, disadvantageously, it has been difficult to achieve excellent insertability into the overtube 6 or into the living body. However, in this embodiment, the length of the rigid part is shortened, and hence insertability is improved. Additionally, since the endoscope 4 is disposed nearer to the distal end, the tip cover 80 or the other elements do not block the visual field of an observation device of the endoscope 4. Therefore, a sufficient visual field can be obtained. A plate member 221 caused to abut against the surface of the end of the endoscope 4 may be used as a restricting member instead of the mark 220, and may be protruded from the tip cover 80 as shown by the broken line in FIG. 7. Additionally, as shown in FIG. 8, an inclined surface 225 is formed by slantingly cutting the corner of the tip cover 80. The inclined surface 225 makes it possible to facilitate a back-and-forth operation, because the suture instrument 1 is contained within the inner diameter of the overtube 6 shown by the phantom line in FIG. 8.

Next, the operation of this embodiment will be described. Although the following description is concerned with a case in which an incision formed in a stomach wall is sutured, a target region is not limited to the stomach wall. Hollow organs, such as the esophagus, duodenum, small intestine, large intestine, womb, or bladder may be targeted. Additionally, a natural opening through which the endoscope 4 is inserted is not limited to the mouth. The nose or anus may be used as the natural opening. Additionally, the treatment instrument of the present invention may be used to suture a mucous-membrane defective part or a perforated part generated by hemostasis or an ulcer.

The endoscope inserting part 5 of the endoscope 4 is passed through the scope holder 26, the valving element 50, and the receiving portion 60 in this order, and then the surface of the end of the endoscope 4 is allowed to coincide with the mark 220. To firmly fix the endoscope 4 to the suture instrument 1, the end of the endoscope 4 and the receiving portion 60 may be fastened together by, for example, a tape. Thereafter, the cartridge 153 is set at a desired position of the suture instrument 1. The overtube 6 is inserted from the mouth of a patient to the neighborhood of the cardiac orifice of the stomach or into the stomach by use of another endoscope. Thereafter, the suture instrument 1 fixed to the endoscope 4 via the overtube 6 is inserted into the stomach.

In the interior of the stomach, the position of the incision of a tissue that is a target region is confirmed by an observation device of the endoscope 4. Since the end of the endoscope 4 is disposed nearer to the distal end of the suture instrument than a conventional endoscope, the visual field is not easily blocked by the suture instrument 1, so that the incision of the tissue and the detachable needle 121 can come within the same visual field.

Figure 16:
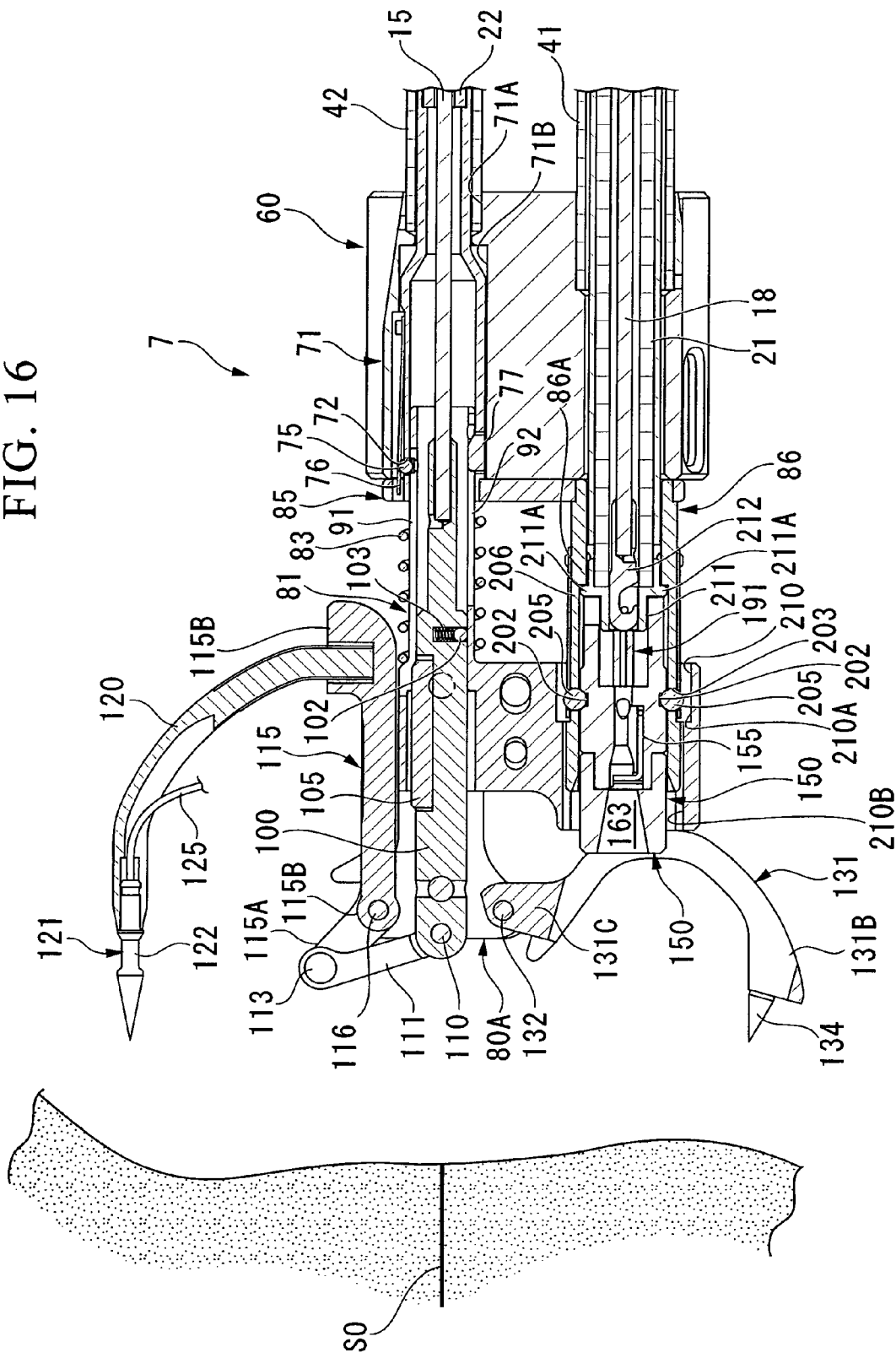
FIG. 16 is a sectional view for illustrating a suture method, showing a state in which a forceps member has been opened toward an incision.

Thereafter, the pair of forceps members 115 and 131 is opened in the interior of the stomach before suturing. In more detail, an operator advances the forceps operating portion 13 of the control portion 2. The forceps operating wire 15 is then advanced, and the link members 111 and 112 connected to the rod 100 allow the forceps members 115 and 131 to pivot on the pins 106 and 132 and be opened. As shown in FIG. 16, when the thus opened forceps members 115 and 131 are allowed to approach the incision SO that is a target region, the pair of forceps members 115 and 131 is closed in such a way as to pinch tissues around the incision SO with the forceps members 115 and 131.

Figure 17:
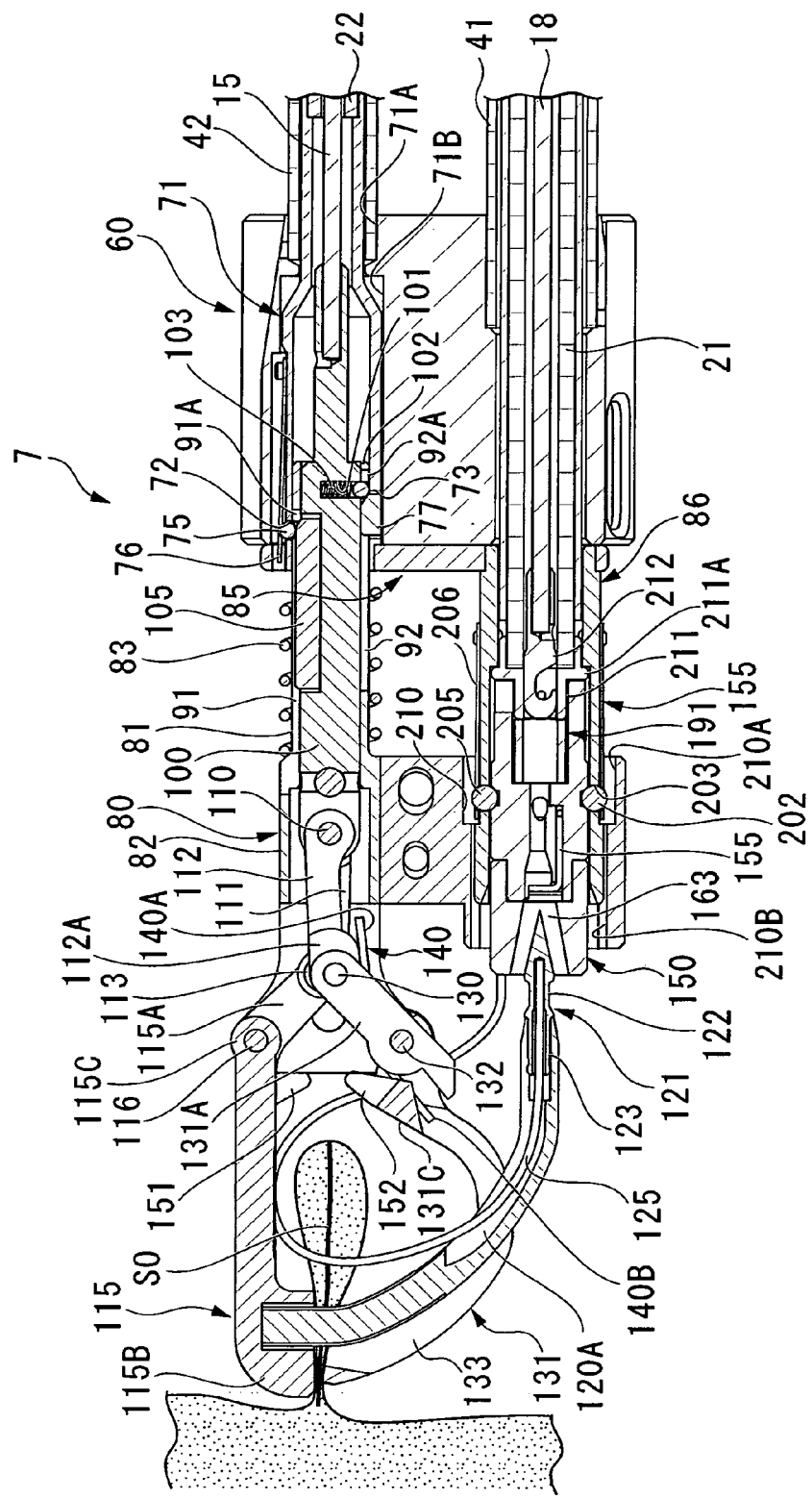
FIG. 17 is a sectional view showing a state in which the forceps member has been closed so as to pinch tissues including the incision.

When the operator allows the forceps operating portion 13 of the control portion 2 to recede therefrom, the forceps operating wire 15 recedes, and the link members 111 and 112 are pulled into the tip cover 80, so that the forceps members 115 and 131 pivot on the pins 106 and 132, respectively, and are closed. The needle 134 of the forceps member 131 is then inserted into the tissue, and presses the tissue against the incision SO. On the other hand, the curved needle 120 of the forceps member 115 is inserted into a tissue on the opposite side of the forceps member 131 with the incision SO therebetween, and is protruded toward the casing 150 through the tissue drawn in by the forceps member 131 across the incision SO. As a result, as shown in FIG. 17, the curved needle 120 and the suture thread 125 are passed through the incision SO.

If the incision SO is relatively large and cannot be pinched by a single suturing operation, it is permissible to first make a puncture in an end of the incision SO, then make a gap between the detachable needle 121 and the needle 134 by widening the curved needle 120 to the extent of about a half, then take a tissue on the opposite side of the incision SO into the gap, and perform a suturing operation while inserting the needle there.

Figure 18:
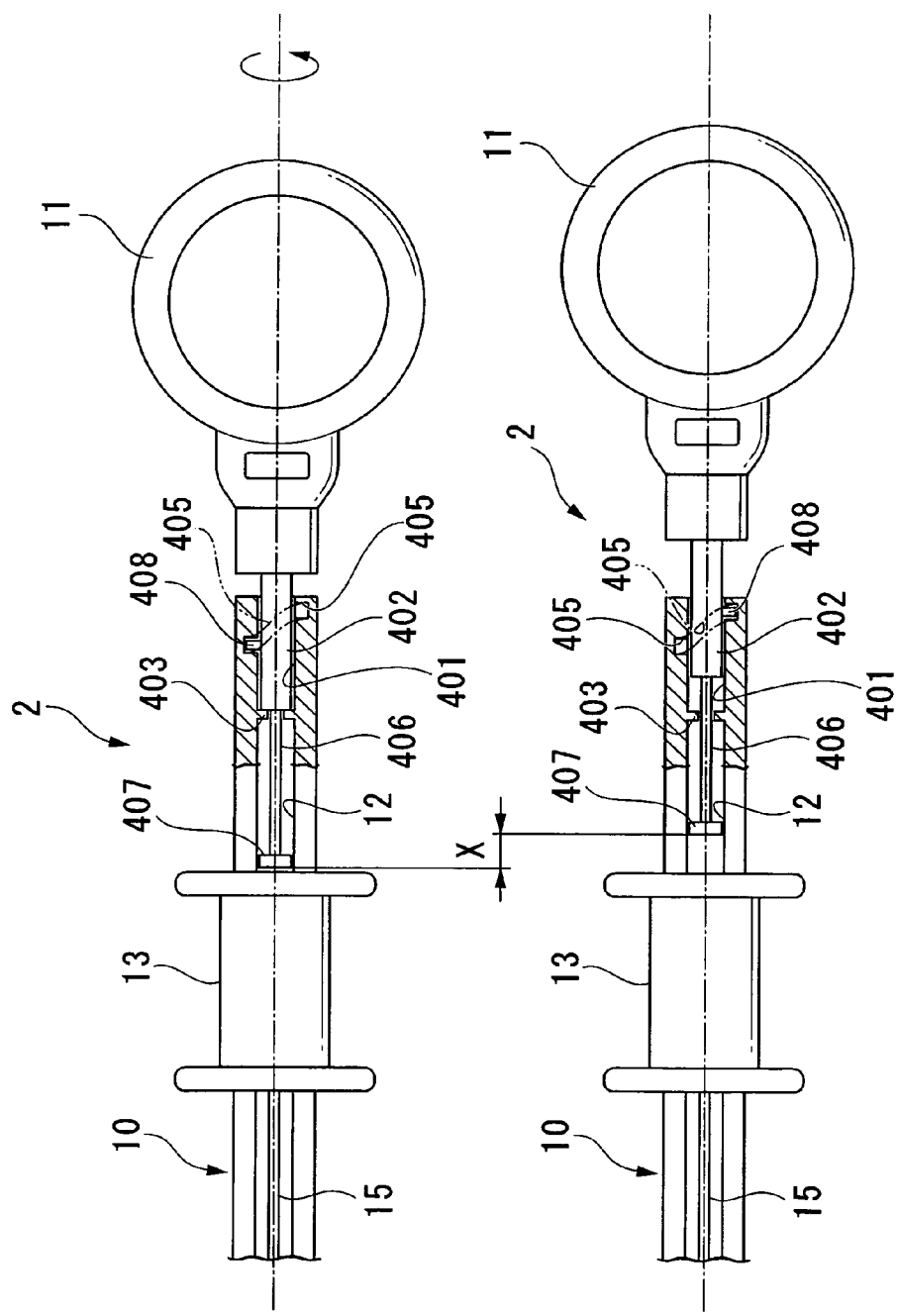
FIG. 18 is a view showing one aspect of the control portion that can reliably perform a needle-inserting operation twice.

If the tissue is hard at this time, the detachable needle 121 cannot be easily inserted through the tissue, and the forceps operating portion 13 cannot be stopped at a position at which the detachable needle 121 arrives through the tissue, because a large force is applied onto the forceps operating portion 13. Accordingly, the detachable needle 121 is often moved, as a serial operation, to a position at which the detachable needle 121 is engaged with the casing 150. If so, the incision cannot be sutured by a twice-inserting operation as described above. To reliably perform the twice-inserting operation, it is recommended to structure the control portion 2 as shown in FIG. 18. In the control portion 2, a hole 401 leading to the slit 12 is formed in the proximal end of the control body 10, and a cam rod 402 extended to the end of the ring 11 is inserted in the hole 401. An abutment portion 403 is disposed at the end of the hole 401 in such a way as to reduce the opening diameter. A spiral cam groove 405 is formed on the inner periphery of the hole 401. The cam groove 405 extends in the circumferential direction with a length greater than at least a semicircle (180 degrees). Further, a rod 406 that can pass through the abutment portion 403 extends from the cam rod 402 toward the distal end. The rod 406 is inside the slit 12, and a stopper 407 is disposed at the tip of the rod 406 so that the stopper 407 can come into contact with the forceps operating portion 13. Further, on the outer periphery of the cam rod 402, a pin 408 extends outwardly in the radial direction. The pin 408 is inserted in the cam groove 405, and the ring 11 is engaged with the control body 10 with the pin 408 therebetween.

In the control portion 2, the forceps operating portion 13 can be pulled until the forceps operating portion 13 comes into contact with the stopper 407. When the ring 11 is rotated from the position shown in FIG. 18 by 180 degrees, the rotational motion of the pin 408 rotating together with the ring 11 is transformed into the linear motion of the ring 11 by the cam groove 405, so that the ring 11 recedes. The stopper 407 formed integrally with the ring 11 recedes by, for example, a movement amount X. Since the stopper 407 recedes, the forceps operating portion 13 can further recede by the movement amount X. If the position obtained at this time is set as a position to which the tip cover 80 is moved until the detachable needle 121 is engaged with the casing 150, and if the first position of the stopper 407 is set as a first position for a twice-inserting operation, the twice-inserting operation will be reliably performed.

Figure 19:
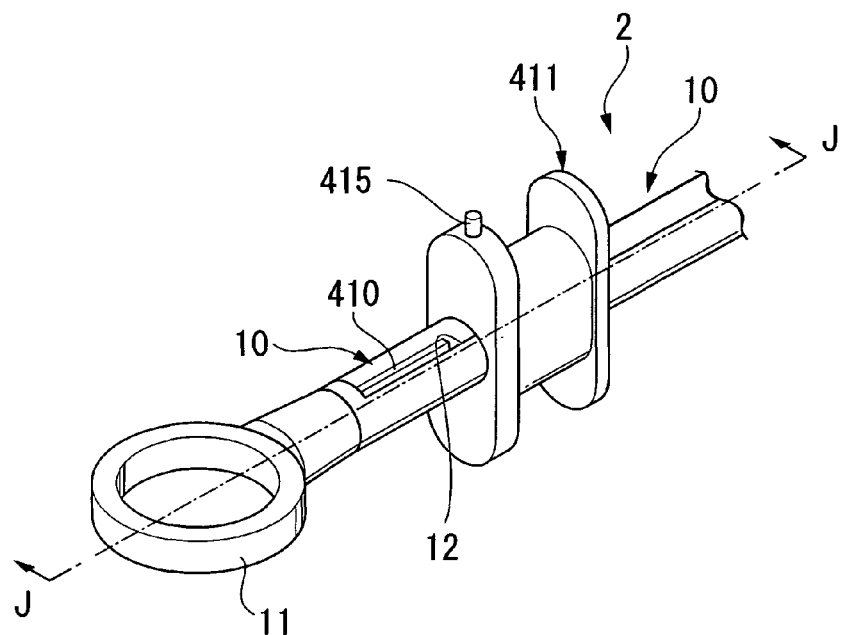
FIG. 19 is a view showing another aspect of the control portion that can reliably perform a needle-inserting operation twice.
Figure 20:
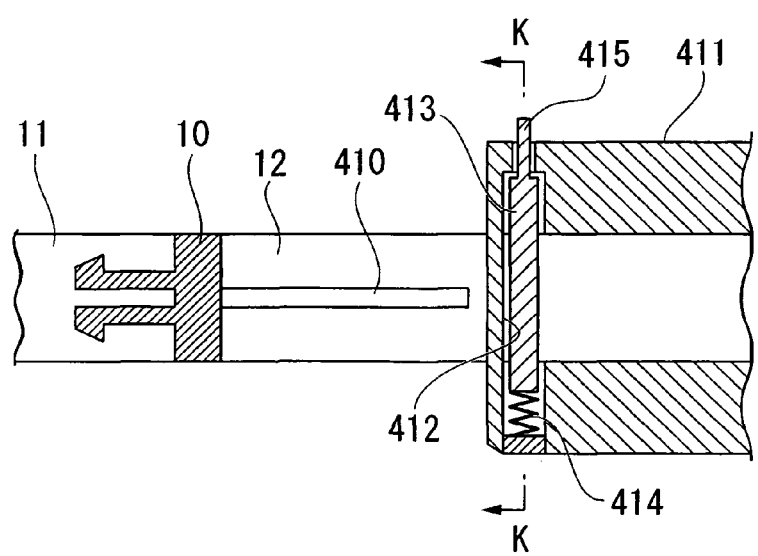
FIG. 20 is a sectional view along line J-J in FIG. 19.
Figure 21:
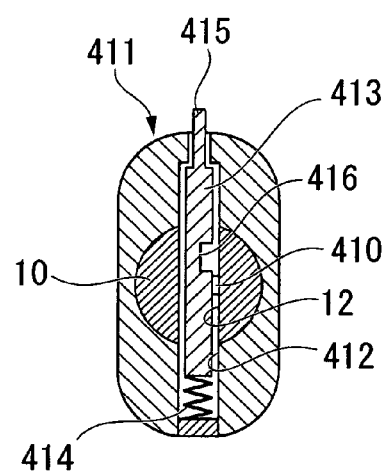
FIG. 21 is a sectional view along line K-K in FIG. 20.
Figure 22:
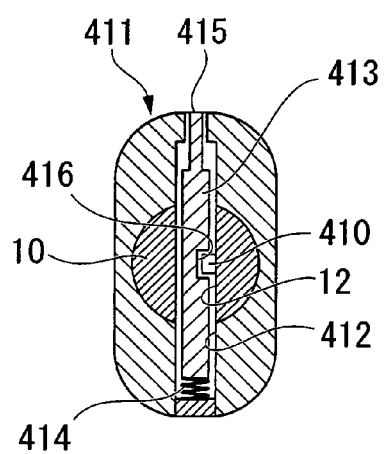
FIG. 22 is a view showing a state in which a stopper releasing button has been pushed from the state in FIG. 21.

Another aspect is shown in FIG. 19. As shown in FIG. 19, an obstacle rail 410 is disposed with a predetermined length in the length direction on the inner surface of the slit 12 of the control body 10 so as to have a ridge toward the inside of the slit 12. A forceps operating portion 411 is attached to the slit 12 slidably back and forth. The forceps operating portion 411 is a slider by which the pair of forceps members 115 and 131 is opened or closed. As shown in FIG. 20, a hole 412 perpendicular in the sliding direction is provided inside. A stopper member 413 is inserted in the hole 412. The stopper member 413 is urged by a coiled spring 414, which is an elastic member, toward an opening narrowed in the hole 412. The end of the stopper member 413 projects from the forceps operating portion 411, and is used as a stopper releasing button 415. The stopper member 413 has a cut 416 formed in the side thereof. As shown in FIG. 21, the cut 416 is sufficiently larger than the obstacle rail 410. However, since the position of the cut 416 does not coincide with the position of the obstacle rail 410 in a natural state, the forceps operating portion 411 can recede only until a stopper 413 comes into contact with the obstacle rail 410. As shown in FIG. 22, when the stopper releasing button 415 is pushed, the stopper 413 is moved in proportion to the shrinkage of the coiled spring 414, and the position of the cut 416 coincides with the position of the obstacle rail 410. Since it becomes possible to avoid the obstacle rail 410 by means of the cut 416, the forceps operating portion 411 can be allowed to further recede toward the ring 11. The movement amount of the forceps operating portion 411 can be controlled by allowing the operator to push the stopper releasing button 415 provided at the end of the stopper 413 as described above, and hence the twice-inserting operation can be reliably performed.

When the curved needle 120 and the suture thread 125 are passed through the incision SO, the forceps member 131 is urged by the urging force of the charging spring 140 in the closing direction, and the needle 134 firmly bites into the tissue. Further, the stoppers 151 and 152 of the forceps members 115 and 131 are pushed against the tip surface 80A of the tip cover 80. As a result, the forceps members 115 and 131 are prevented from sagging, and the axial line of the detachable needle 121 and the axial line of the casing 150 substantially coincide with each other.

Figure 23:
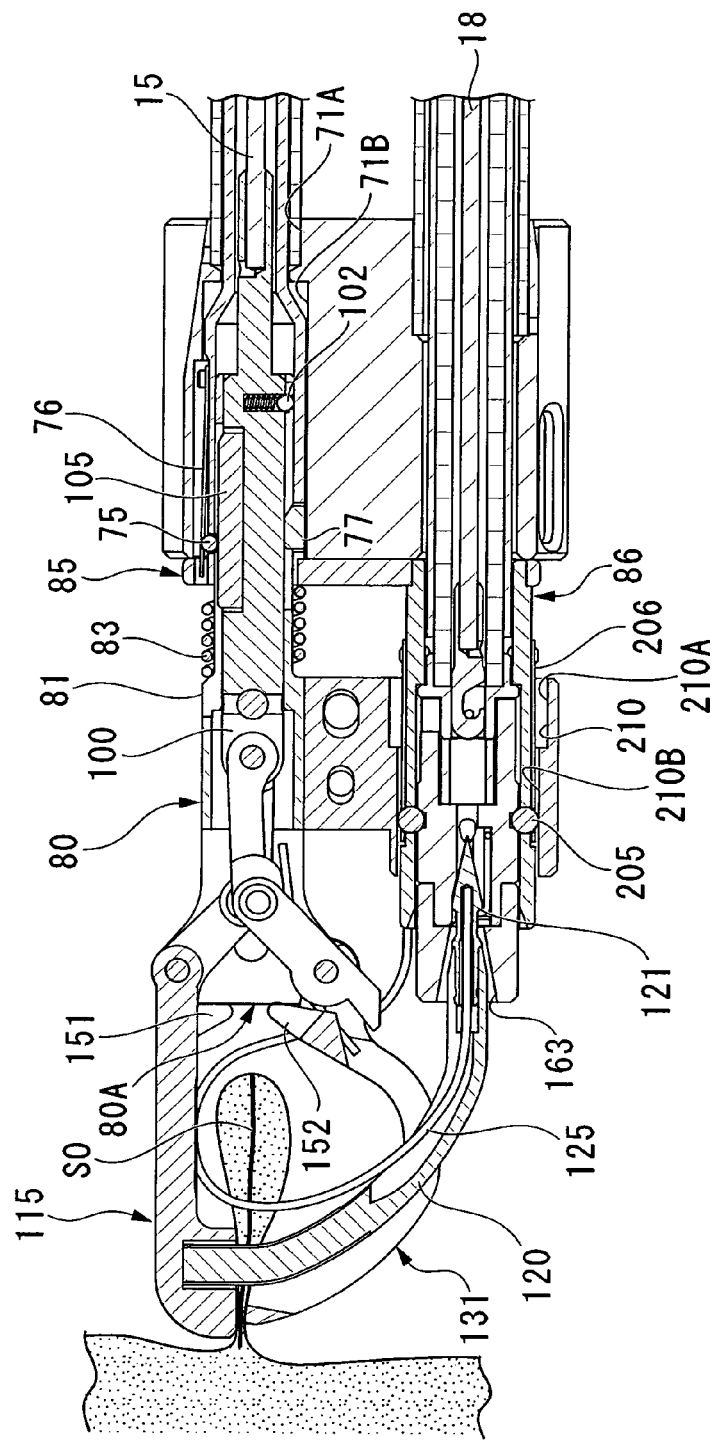
FIG. 23 is a sectional view showing a state in which the detachable needle has been inserted into the casing by pulling a tip cover and the forceps member.

When the pair of forceps members 115 and 131 is completely closed, or immediately before the pair of forceps members 115 and 131 is completely closed, the tapered surface of the release member 105 of the rod 100 pulled into the tube part 81 of the tip cover 80 pushes the pin 75 up. The engagement between the tube part 81 and the distal-end supporting portion 71 is released by pushing the pin 75 up. As a result, the tip cover 80 can be pulled into the distal-end supporting portion 71. Therefore, when the forceps operating wire 15 is allowed to further recede as shown in FIG. 23, the tip cover 80 recedes while compressing the coiled spring 83, and the forceps members 115 and 131, which are connected to the tip cover 80 by means of the pins 116 and 132 and the stoppers 151 and 152, recede. At this time, the ball 102 of the tube part 81 enters the large-diameter part 92A beyond the release member 77, and the tube part 81 and the rod 100 are connected together.

On the other hand, the casing 150 is held by the casing supporting member 86, and is not moved. Moreover, the outer periphery of the ball 205 engaged with the casing 150 is covered with the small-diameter part 210B of the guide hole 210 by allowing the tip cover 80 to recede, and hence the ball 205 cannot be moved outwardly in the radial direction. As a result, in a state of preventing the movement of the casing 150, the detachable needle 121 attached to the tip of the curved needle 120 is inserted in the casing 150. In the reception hole 163, the detachable needle 121 is locked to the casing 150 by the wire spring 165.

When the forceps operating wire 15 is completely pulled, the forceps operating portion 13 is advanced. The tip cover 80 starts moving to the original position by the restoring force of the coiled spring 83 disposed outside the tube part 81. At this time, the tip cover 80 and the rod 100 are advanced together since the tube part 81 and the rod 100 are connected together by means of the ball 102 entering the large-diameter part 92A of the slit 92. Therefore, the pair of forceps members 115 and 131 is advanced without being opened, and the curved needle 120 attached to the forceps member 115 makes a parallel movement so as to recede from the casing 150.

Figure 24:
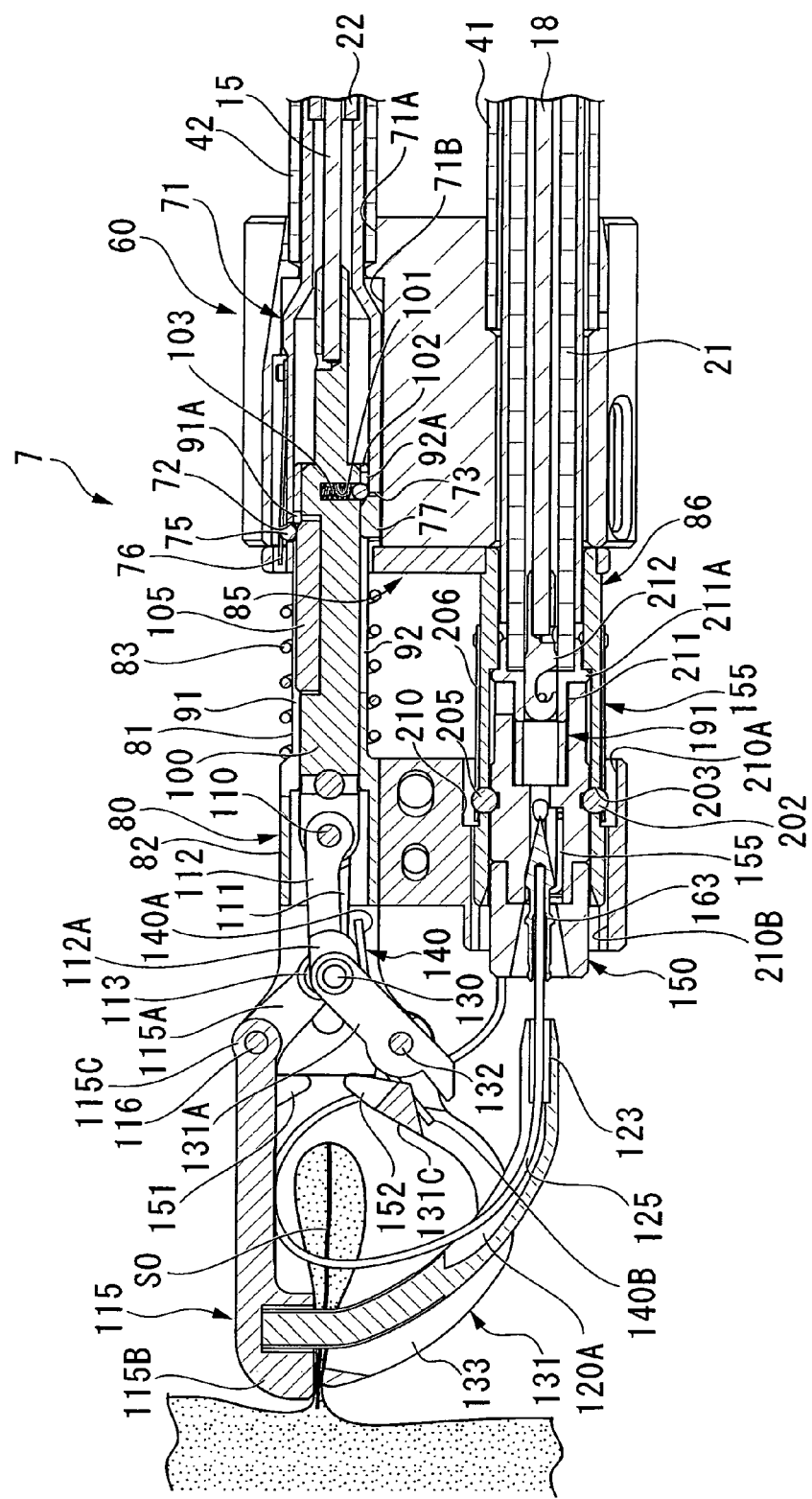
FIG. 24 is a view showing a state in which the detachable needle contained in the casing has been detached from a curved needle by returning the tip cover and the forceps member toward the distal end.
Figure 25:
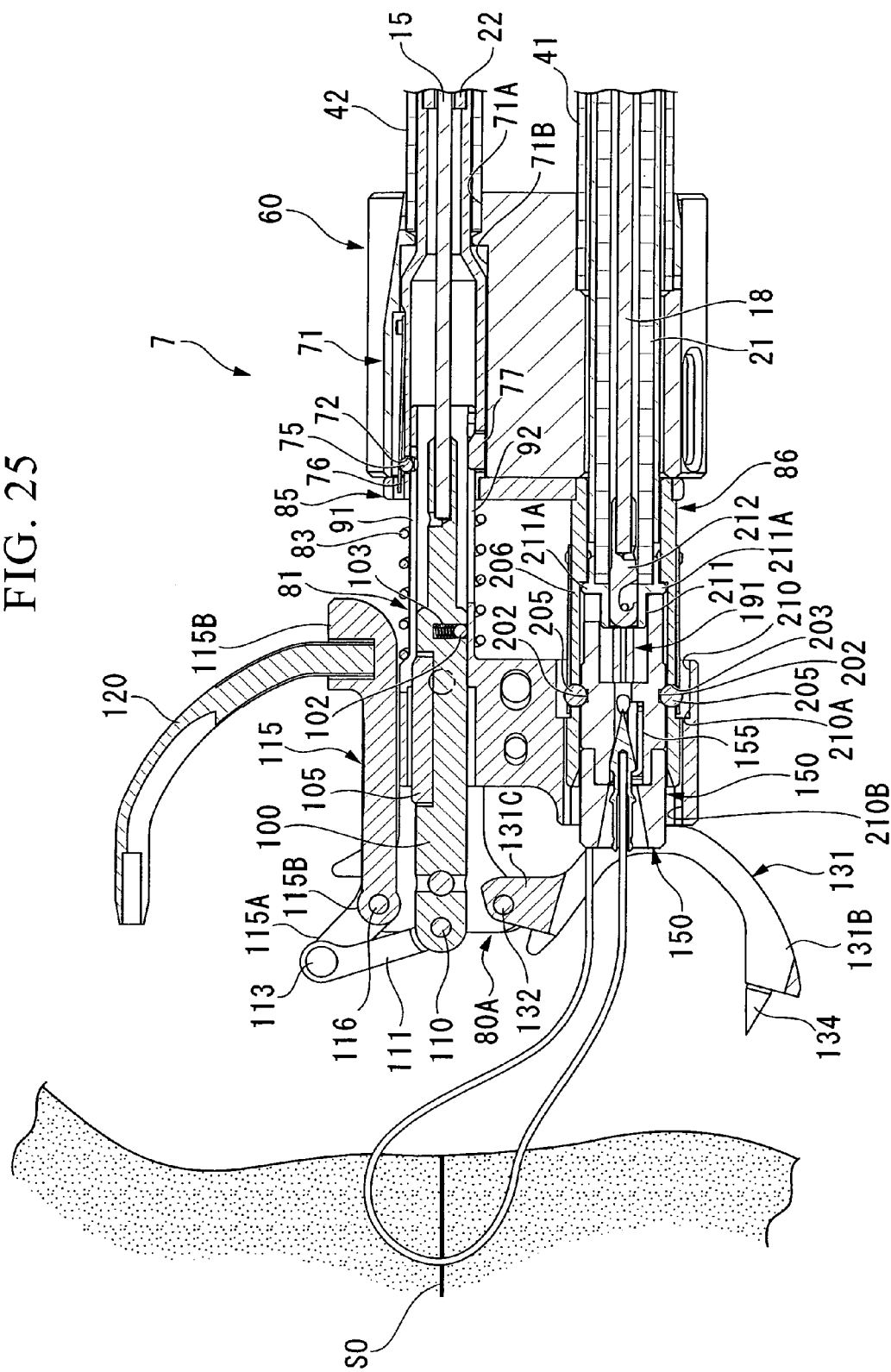
FIG. 25 is a view showing a state in which the forceps member has been opened after detaching the detachable needle from the curved needle.

The detachable needle is disengaged from the curved needle 120 by this parallel movement. As shown in FIG. 24, the detachable needle 121 stays while being contained in the casing 150, and the curved needle 120 recedes from the casing 150. Since the pair of forceps members 115 and 131 has not yet opened at this time, interference never occurs between the curved needle 120 and the casing 150. Thereafter, the ball 102 proceeding together with the tube part 81 of the tip cover 80 is brought into contact with the release member 77, and is pushed into the rod 100 by the tapered surface of the proximal end of the release member 77. Thereby, the engagement between the rod 100 and the tube part 81 is released, and the rod 100 becomes capable of proceeding to the tip cover 80. As a result, when the forceps operating portion 13 is advanced, the pair of forceps members 115 and 131 can be opened. As shown in FIG. 25, the curved needle 120 is pulled out from the tissue by opening the pair of forceps members 115 and 131. The suture thread 125 remains like a loop while being passed through the tissue.

Figure 26:
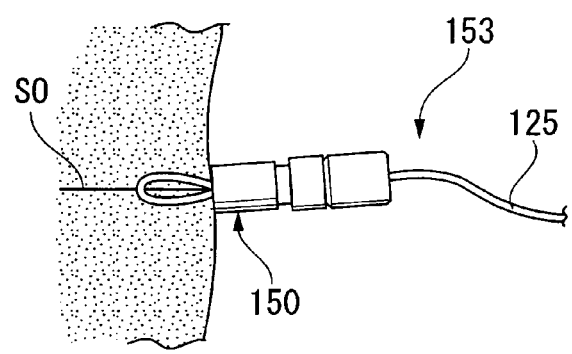
FIG. 26 is a view showing a state in which the treatment instrument is retained while the incision has been sutured.

When the suture thread 125 is tightened, the hook sheath 21 is advanced. The hook sheath 21 pushes the distal claw portion 211, and the distal claw portion 211 pushes the casing 150 from the tip cover 80 toward the tissue. Since the tip cover 80 has returned to the original position, the diameter-increased part 210A of the guide hole 210 is present around the ball 205, and the ball 205 is disengaged from the concave portion 202 by the elastic deformation of the leaf spring 206, so that the engagement between the casing 150 and the casing supporting member 86 is released. When the casing 150 is protruded from the casing supporting member 86, the hook operating portion 14 is allowed to recede, and the hook 212 is allowed to recede. Since the suture thread 125 engaged with the hook 212 is pulled out, the loop of the suture thread 125 passing through the tissue is narrowed down. Since the handle 16 of the hook operating portion 14 can be pulled beyond the forceps operating portion 13, the suture thread 125 can be pulled out until the casing 150 is brought into contact with the tissue. As a result, as shown in FIG. 26, the incision SO is sutured by the cartridge 153. In a state in which the incision SO has been sutured, the cartridge 153 is retained in the body by releasing the engagement of the hook 212 or by cutting the suture thread 125 extending from the casing 150 by use of a known thread-cutting treatment device being passed through an operating channel of the endoscope 4.

In this embodiment, the structure is formed so that the engagement between the distal-end supporting portion 71 and the tip cover 80 can be released by providing the pin 75 that is a first locking member in the process of allowing the forceps operating wire 15 to recede. Therefore, the detachable needle 121 can be inserted into the casing 150 in accordance with an operation in which the pair of forceps members 115 and 131 is closed while pulling the forceps operating wire 15. A conventional control portion is complex in structure, and requires much skill in operating. However, in this embodiment, the work including the engagement of the detachable needle 121 can be achieved by a series of operations of the forceps operating portion 13, and hence the instrument can be easily operated. In other words, for example, in the treatment instrument described by US2003-0181924A1, the hook sheath holding the casing must be moved back and forth to engage the detachable needle with the casing. To do so, the control portion must be shifted from one hand to the other. Additionally, to engage the detachable needle with the casing, the detachable needle and the center axis in the longitudinal direction of the casing must coincide with each other. Therefore, an operator must confirm this coincidence during an operation. In contrast, in this embodiment, since the engagement between the distal-end supporting portion 71 and the tip cover 80 is released when a state in which the tip of the detachable needle 121 can be engaged with the casing 150 is reached, the detachable needle 121 can be inserted into the casing 150 in response to the closing motion of the pair of forceps members 115 and 131. Therefore, operability is improved. In this embodiment, the suture instrument is disclosed as an example of a treatment instrument. However, without being limited to this, the present invention can be applied to biopsy forceps or grasping forceps that are different in shape from the forceps members 115 and 131. If the present invention is applied to biopsy forceps, it will become possible to perform the operation of pinching tissues and the operation of removing the tissues, as a series of operations, by an operation performed on the side of the proximal end of the instrument. If the present invention is applied to grasping forceps, it will become possible to perform the operation of pinching tissues and the operation of transferring the tissues, as a series of operations, by an operation performed on the side of the proximal end of the instrument.

Additionally, the structure is formed so that the link mechanism of the forceps members 115 and 131 and the tip cover 80 can be advanced together by providing the ball 102 that is a second locking member before the pair of forceps members 115 and 131 is opened. Therefore, the pair of forceps members 115 and 131 can be kept closed until the curved needle 120 is completely disengaged from the casing 150. Since the possibility that interference will occur between the curved needle 120 and the casing 150 is removed, the pair of forceps members 115 and 131 is reliably opened and closed. Additionally, both the disengagement of the detachable needle 121 from the curved needle 120 and the opening motion of the pair of forceps members 115 and 131 are accomplished by a series of operations of the forceps operating portion 13, and hence the instrument can be easily operated.

Since the ball 205 by which the casing 150 and the casing supporting member 86 are engaged together is provided as a third locking member, and since the engagement of the ball 205 is controlled by the guide hole 210 of the tip cover 80, the casing 150 can be reliably fixed, and the detachable needle 121 can be easily engaged with the casing 150.

Since the stoppers 151 and 152 that are brought into contact with the tip surface 80A of the tip cover 80 are provided on the forceps members 115 and 131, the deviation of the axis of the curved needle 120 can be prevented when the pair of forceps members 115 and 131 is closed. If the deviation of the axis of the curved needle 120 occurs, it will become difficult to insert the detachable needle 121 into the casing 150 or to detach the detachable needle 121 from the curved needle 120. However, in this embodiment, these problems are solved.

Since the movement control portion 25 and the scope holder 26 are provided in the path of the insertion portion 3, and since only the hook sheath 21 or both of the sheaths 21 and 22 are formed to simultaneously move back and forth, the control portion can be more easily operated than a conventional control portion, and the sheath that is moved back and forth by an operator can be easily imagined, thus making it easy to become skillful in operating. Additionally, since the movement control portion 25 is away from the control body 10, it is easy to share the operations.

Since the control portion (the forceps operating portion 13) that operates the forceps members 115 and 131 and the other control portion (the hook operating portion 14) that operates the hook 212 are integrally provided in the control portion 2, the control portions can be made compact, and can be easily handled. Since the hook operating portion 14 is disposed on the side of the distal end of the instrument, and since the forceps operating portion 13 is formed to enter the space between the handles 16, the stroke of the hook operating portion 14 can be enlarged, and the suture thread 125 can be easily tightened.

Various modifications of the suture instrument 1 will be shown hereinafter.

Figure 27:
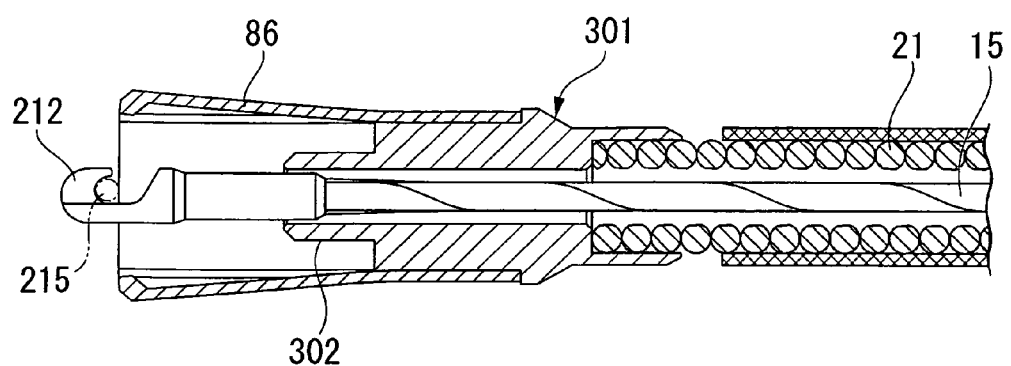
FIG. 27 is a sectional view showing a distal claw portion formed integrally.

As shown in FIG. 27, a distal claw portion 301 is fixed to the distal end of the hook sheath 21, and the hook operating wire 18 is drawn therein. Further, the distal claw portion 301 is fixed to the casing holding portion (whose end is slightly opened outwardly in the radial direction so as to receive the casing 150) 86. A claw portion 302 is formed integrally with the tip of the distal claw portion 301, by which the proximal end of the casing 150 can be locked. The distal claw portion 301 is formed by molding the distal claw portion 211 and the step 86A of the casing supporting member 86 that receives the distal claw portion 211 integrally with each other as shown in FIG. 9, and hence both manufacturing costs and the number of assembling steps can be reduced.

Figure 28:
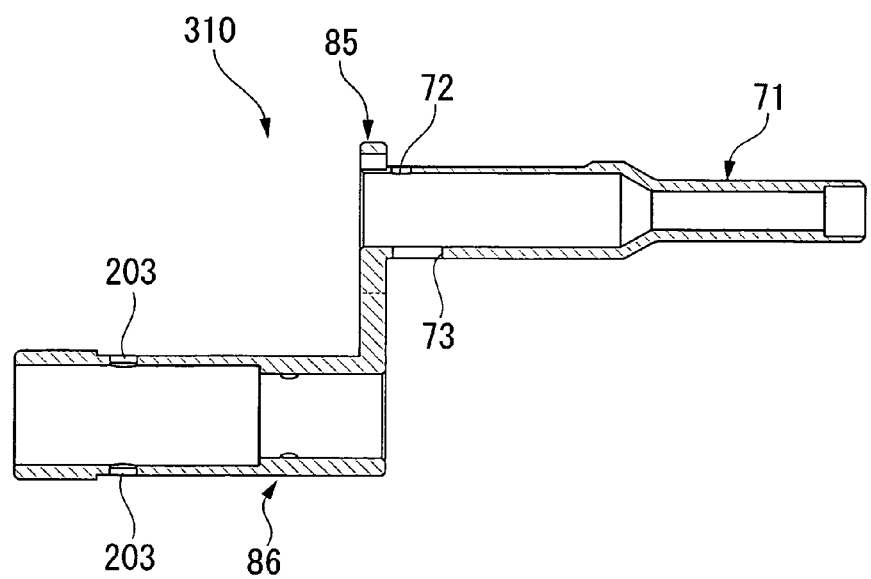
FIG. 28 is a view showing a structure in which a distal-end supporting portion, a bridge portion, and a casing holding portion are formed integrally with each other.

As shown in FIG. 28, it is permissible to use a supporting member 310 formed by integrally molding the distal-end supporting portion 71, the bridge portion 85, and the casing supporting member 86. The supporting member 310 is bent like a crank as a whole, and can make component costs and assembly costs lower than a structure in which the distal-end supporting portion 71 and the casing supporting member 86 are formed individually. Metal injection molding, turning center, molding, casting, or forging can be used as the producing method.

Figure 29:
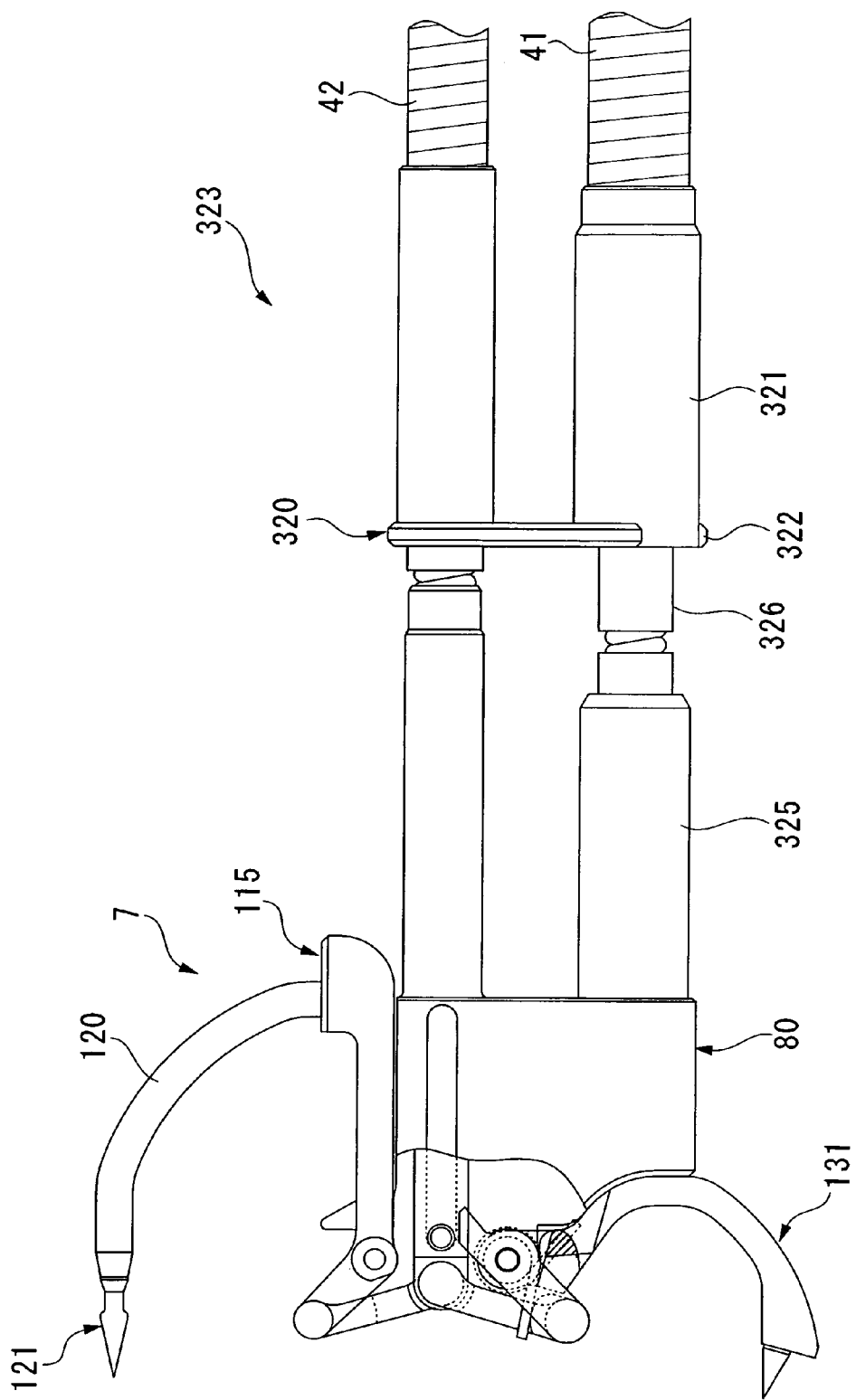
FIG. 29 is a view showing a distal end of a suture instrument according to another embodiment, in which a receiving portion is provided with a cut.

As shown in FIG. 29, in a receiving portion 320, a cut 322 may be formed in a part that is engaged with an outer member 321 to which the tip of the coil sheath 41 is fixed. The receiving portion 320 is used to fix the distal end of the endoscope 4 to a suture instrument 323. The receiving portion 320 holds the outer member 321 substantially in the cross-sectional shape of the letter C by means of the cut 322. The position of the cut 322 is a position at which the endoscope 4 and the suture instrument 323 are brought into contact with or close to the inner surface of the overtube 6 when the endoscope 4 and the suture instrument 323 are combined together and are inserted into the overtube 6. The outer diameter obtained by combining the endoscope 4 and the suture instrument 323 together can be reduced by cutting the receiving portion 320 at this position, and the insertion into the overtube 6 can be easily carried out. The suture instrument 323 has a structure in which the distal claw portion 301 that is engaged with the casing 150 is moved back and forth by a sheath 326. The distal claw portion 301 is moved back and forth inside the tip cover 80 and a casing holding portion 325 formed integrally with the tip cover 80.

Figure 30:
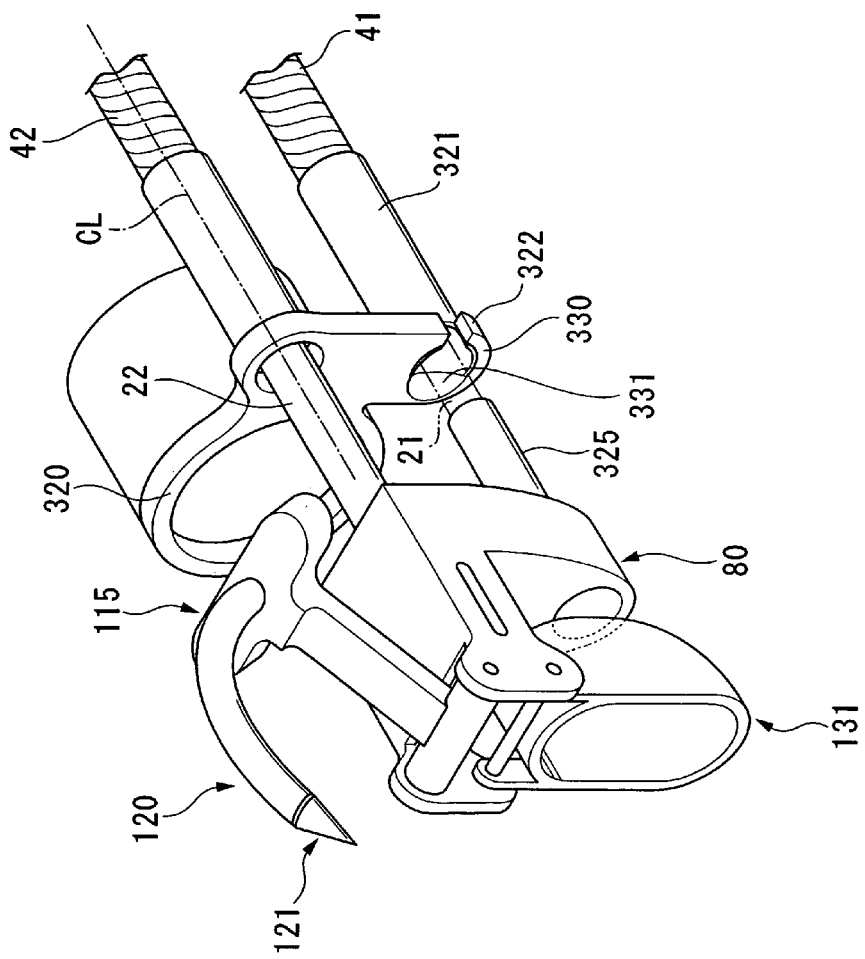
FIG. 30 is a view showing a receiving portion provided with a cut and a tapered surface.

As shown in FIG. 30, in the receiving portion 320, a holding portion 330 holding the outer member 321 has the cut 322 so that the cross section thereof has the shape of the letter C, and a tapered surface 331 that is opened toward the distal end is provided. The tapered surface 331 has a curved surface in which the axis line CL of the coil sheath 42 is a center axis. When the tip cover 80 is allowed to recede by operating the hook sheath 21 and the forceps sheath 22, the proximal end of the casing holding portion 325 is not caught by the receiving portion 320, and hence the tip cover 80 can be smoothly moved back and forth.

Although the preferred embodiments have been described as above, the present invention is not limited to these. For example, the present invention can be applied to a rigid endoscope having a rigid insertion portion although a description has been given of a use for the flexible endoscope having the flexible insertion portion in the above embodiments. Various structural additions, exclusions, replacements, and other exchange forms can be executed within the scope not departing from the spirit of the present invention. The present invention is not limited by the above description, and is limited only by the appended claims.

What is claimed is:

1. An endoscopic treatment instrument comprising:
    an insertion portion having a distal end and a proximal end, the distal end capable of being inserted into a body;
    a treatment portion provided at the distal end of the insertion portion; and
    a control portion provided at the proximal end of the insertion portion;
    wherein the treatment portion includes:
    a pair of forceps members;
    a tip cover which supports a pivot shaft that pivots at least one of the pair of forceps members openably and closably with respect to the other forceps member;
    a distal end holding portion that is fixed to the distal end of the insertion portion and in which the tip cover is held relatively movably toward the distal end of the insertion portion and toward the proximal end of the insertion portion;
    a distal end locking member that restrains a relative movement by locking the tip cover onto the distal end holding portion when the pair of forceps members is opened to grasp a specified object;
    a manipulating member disposed at the insertion portion and opens and closes the pair of forceps members; and
    a distal end release member that is provided on the distal end of the insertion portion by which the pair of forceps members is opened and closed and that releases an engagement made by the distal end locking member between the tip cover and the distal end holding portion at least when the pair of forceps members is closed;
    a forceps locking member connecting the tip cover and the pair of forceps members together and being disposed so as to advance the tip cover and a part of forceps members together; and
    a forceps release member that releases connection between the forceps members and the tip cover after an engagement made by the distal end locking member is released;
    an attaching portion provided at the forceps members so that a tip member of a retaining device is detachably attached and the retaining device including the tip member attached to an end of a string member, a hook catching portion provided at an opposite end of the string member;
    a casing that is provided between the end of the string member and the opposite end thereof and that is capable of being engaged with the tip member;
    a locking member that is provided at the casing and that restrains movement of the casing between the end of the string member and the opposite end thereof;
    a casing holding portion that is capable of detachably holding the casing and that is provided at the distal end holding portion; and a casing locking member that engages the casing with the casing holding portion;

a guide portion, expanding at a proximal side of the guide portion, provided at the tip cover, and controlling an engagement state made by the casing locking member between the casing holding portion and the casing;

wherein the distal end release member releases an engagement made by the distal end locking member between the tip cover and the distal end holding portion when the tip member reaches a state of being able to be engaged with the casing in response to a closing motion of the pair of forceps members; and wherein the casing holding portion is inserted into the guide portion to advance and retract, the casing holding locking member can be radially-outwardly movable at the expanding portion of the proximal side of the guide portion and cannot be moved outwardly at a distal side of the guide portion due to a narrow inside of the distal side of the guide portion.

2. The endoscopic treatment instrument according to claim 1, further comprising stoppers each of which is provided at each of the forceps members, the stoppers being brought into contact with the tip cover when the pair of forceps members is closed.

3. The endoscopic treatment instrument according to claim 1, wherein the control portion includes:

a forceps operating portion that opens and closes the pair of forceps members;

a hook operating portion used to operate a hook with which the hook catching portion of the retaining device can be engaged; and a control body that has a shaft which slidably supports the forceps operating portion and the hook operating portion.

4. The endoscopic treatment instrument according to claim 3, wherein the hook operating portion includes at least one finger hook portion that is supported by the shaft nearer to a distal end in an insertion direction than the forceps operating portion and that extends toward a proximal end in the insertion direction, the hook operating portion being slidably supported so as to be overlapped with the forceps operating portion at a position at which the finger hook portion is more away from the shaft than the forceps operating portion.

5. The endoscopic treatment instrument according to claim 1, further comprising:

a receiving portion that holds a rigid part of a distal end of an insertion part of an endoscope; and a regulating member that regulates a position of the distal end of the endoscope, which is protruded from the receiving portion and is held, at a relative position with respect to the tip cover.

6. The endoscopic treatment instrument according to the claim 5, wherein the receiving portion has a C-shaped base into which an endoscope inserting part of the endoscope can be inserted.

7. The endoscopic treatment instrument according to claim 1, further comprising:

a valving element that has through-holes through which an insertion part of an endoscope and the insertion portion are inserted, in order to insert the insertion portion into an overtube along the insertion part of the endoscope, the valving element including a tapered surface provided at an opening of the through-hole and a contact part that comes into contact with an inner surface of the overtube.

8. The endoscopic treatment instrument according to claim 1, wherein the insertion portion includes:

a first sheath through which a first wire used to open and close the pair of forceps members is passed movably back and forth toward the distal end and toward the proximal end;

a second sheath through which a second wire to an end of which a hook capable of being engaged with the hook catching portion of the retaining device is connected is passed movably back and forth toward the distal end and toward the proximal end;

a first holder which bundles the first sheath and the second sheath together;

a second holder which bundles the first sheath and the second sheath together and that is provided nearer to the distal end than the first holder;

a first adjusting member that provides sliding friction to the second sheath with respect to the first holder; and a second adjusting member that provides smaller sliding friction than the first adjusting member to the first sheath with respect to the second holder.

9. The endoscopic treatment instrument according to claim 1, wherein the control portion includes:

a forceps operating portion used to open and close the pair of forceps members;

a hook operating portion used to operate a hook with which the hook catching portion of the retaining device can be engaged; and a control body that disposes the forceps operating portion and the hook operating portion slidably on one axis.

10. The endoscopic treatment instrument according to claim 9, wherein the hook operating portion is disposed nearer to the distal end in the insertion direction than the forceps operating portion, the hook operating portion has a plurality of finger hook portions that extend toward the proximal end in the insertion direction, and the forceps operating portion can enter a space between the finger hook portions.

11. The endoscopic treatment instrument according to claim 9, wherein the insertion portion includes:

a first sheath through which a first wire used to open and close the pair of forceps members is passed movably back and forth toward the distal end and toward the proximal end;

a second sheath through which a second wire to an end of which a hook capable of being engaged with the hook catching portion of the retaining device is connected is passed movably back and forth toward the distal end and toward the proximal end;

a first holder which bundles the first sheath and the second sheath together;

a second holder which bundles the first sheath and the second sheath together and that is provided nearer to the distal end than the first holder;

a first adjusting member that provides sliding friction to the second sheath with respect to the first holder; and a second adjusting member that provides smaller sliding friction than the first adjusting member to the first sheath with respect to the second holder.

12. The endoscopic treatment instrument according to claim 1, wherein the control portion includes:

a forceps operating portion used to open and close the pair of forceps members;

a hook operating portion used to operate a hook with which the hook catching portion of the retaining device can be engaged; and a control body that disposes the forceps operating portion and the hook operating portion slidably on one axis.

13. The endoscopic treatment instrument according to the claim 1, wherein the tip cover has a concave part so as to prevent a bump between the tip cover and the forceps member from being made.

14. The endoscopic treatment instrument according to claim 1, further comprising:
a distal-end supporting portion into which the tip cover is inserted,
wherein the tip cover includes an elastic member disposed outside of the tip cover for urging so as to separate the tip cover from the distal-end supporting portion.

15. The endoscopic treatment instrument according to the claim 14, wherein the elastic member is a spring.

16. An endoscopic treatment instrument comprising:
a pair of forceps members, at least one of which is pivoted openably and closably with respect to the other of the pair of forceps members,
a casing holding portion that is provided at a distal end of an insertion portion to be inserted into a body and that holds a casing connected to a tip member by a thread, the casing containing the tip member detachably attached to one of the pair of forceps members after being passed through a tissue in response to a closing motion of the pair of forceps members;
a casing locking member, holding in the casing, and engaging the casing holding portion and the casing together;
a guide member that controls an engagement state made by the casing locking member between the casing holding portion and the casing;
a tip cover including a tube part, the casing holding portion, the guide member and a forceps operating member being inserted through the tip cover;
a small-diameter part and a large-diameter part disposed on an inner peripheral surface of the tube part; and
a controlling mechanism that is provided in the forceps operating member that can be extended and contracted, that protrudes in a radially-outwardly direction of the forceps operating member, and that controls a connection state between the forceps operating member and the tip cover, wherein the connection state is made by being inserted into the forceps operating member with a push from the small-diameter part or by being inserted into the large-diameter part based on the forceps operating member advancing and retreating.

17. An endoscopic treatment instrument comprising:
a pair of forceps members;
a tip cover which has a concave part on a peripheral surface of a distal end thereof and which supports a pivot shaft that pivots at least one of the pair of forceps members openably and closably with respect to the other forceps member;
an uneven member having at least a portion disposed within the concave part, which is supported by the pivot shaft at a proximal side of at least one of the pair of forceps members, and which is disposed at a boundary between the tip cover and the pair of forceps members;
a pair of stoppers provided between the pair of forceps members, the pair of stoppers contacting the tip cover with a proximal side of the pair of forceps members;
a receiving portion that detachably holds a side of a distal end of an endoscope to be inserted into a body; and
a regulating member that regulates a position of the distal end of the endoscope at a relative position with respect to the tip cover in order to restrict an amount of projection of the distal end of the endoscope with respect to the receiving portion.

18. An endoscopic treatment instrument comprising:
a first sheath and a second sheath to a distal end of each of which a treatment portion used to perform treatment is connected and to a proximal end of each of which a control portion that operates the treatment portion is connected;
a first holder which bundles the first sheath and the second sheath together;
a first adjusting member that provides sliding friction to the second sheath with respect to the first holder, the first sheath being fixed with the first holder in one, the second sheath being movably held by the first holder via the first adjusting member which provides sliding friction to the second sheath;
a second holder which bundles the first sheath and the second sheath and that is provided nearer to the distal end than the first holder; and
a second adjusting member that provides smaller sliding friction than the first adjusting member to the first sheath with respect to the second holder, the first sheath being movably held by the second holder via the second adjusting member which provides sliding friction to the first sheath, and the second sheath is movably held by the first holder.

19. The endoscopic treatment instrument according to claim 18, wherein a first wire to actuate the treatment portion is passed through the first sheath, and a second wire to actuate the treatment portion is passed through the second sheath.

20. The endoscopic treatment instrument according to claim 19, wherein the first wire is a forceps operating wire used to open and close at least one of a pair of forceps members provided at the treatment portion with respect to the other forceps member.

21. The endoscopic treatment instrument according to claim 18, wherein the control portion includes:
a forceps operating portion used to open and close a pair of forceps members;
a hook operating portion used to operate a hook for tightening a suture thread; and
a control body that disposes the forceps operating portion and the hook operating portion slidably on one axis.

22. The endoscopic treatment instrument according to claim 21, wherein the hook operating portion is disposed nearer to the distal end in an insertion direction than the forceps operating portion, the hook operating portion has a plurality of finger hook portions that extend toward the proximal end in the insertion direction, and the forceps operating portion can enter a space between the finger hook portions.

* * * * *